(12) United States Patent
Holmdahl

(10) Patent No.: US 10,774,129 B2
(45) Date of Patent: Sep. 15, 2020

(54) COMPLEXES OF TYPES OF MHC CLASS II THAT BIND TO COLLAGEN TYPE II PEPTIDES AND THEIR USE ON DIAGNOSIS AND TREATMENT

(71) Applicant: FRAUNHOFER-GESELLSCHAFT ZUR FÖRDERUNG DER ANGEWANDTEN FORSCHUNG E.V., Munich (DE)

(72) Inventor: Rikard Holmdahl, Stockholm (SE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 364 days.

(21) Appl. No.: 14/953,484

(22) Filed: Nov. 30, 2015

(65) Prior Publication Data

US 2016/0130323 A1 May 12, 2016

Related U.S. Application Data

(63) Continuation of application No. 14/009,886, filed as application No. PCT/SE2012/005378 on Apr. 5, 2012.

(60) Provisional application No. 61/472,122, filed on Apr. 5, 2011.

(30) Foreign Application Priority Data

Apr. 5, 2011 (SE) ........................ 1150297

(51) Int. Cl.
| | |
|---|---|
| *C07K 14/78* | (2006.01) |
| *G01N 33/564* | (2006.01) |
| *G01N 33/569* | (2006.01) |
| *C07K 14/47* | (2006.01) |
| *C07K 19/00* | (2006.01) |
| *C07K 14/74* | (2006.01) |
| *A61K 39/00* | (2006.01) |
| *C12N 9/88* | (2006.01) |
| *A61K 38/00* | (2006.01) |
| *A61K 35/12* | (2015.01) |

(52) U.S. Cl.
CPC ............ *C07K 14/78* (2013.01); *A61K 39/001* (2013.01); *A61K 39/0008* (2013.01); *C07K 14/47* (2013.01); *C07K 14/70539* (2013.01); *C07K 19/00* (2013.01); *C12N 9/88* (2013.01); *C12Y 402/01011* (2013.01); *G01N 33/564* (2013.01); *G01N 33/56977* (2013.01); *A61K 38/00* (2013.01); *A61K 2035/122* (2013.01); *G01N 2333/525* (2013.01); *G01N 2333/54* (2013.01); *G01N 2333/57* (2013.01); *G01N 2333/7051* (2013.01); *G01N 2333/70514* (2013.01); *G01N 2333/70539* (2013.01); *G01N 2333/70575* (2013.01); *G01N 2333/988* (2013.01); *G01N 2800/102* (2013.01); *G01N 2800/24* (2013.01)

(58) Field of Classification Search
None
See application file for complete search history.

(56) References Cited

FOREIGN PATENT DOCUMENTS

| | | | |
|---|---|---|---|
| EP | 1332760 | | 8/2003 |
| JP | 08151396 A | * | 6/1996 |
| WO | 03/050542 | | 6/2003 |
| WO | 2007/017556 | | 2/2007 |
| WO | 2007/123976 | | 11/2007 |
| WO | 2008/090360 | | 7/2008 |

OTHER PUBLICATIONS

Cecconi, V., et al. Cytometry Part A, 2008; 73A:1010-1018.*
Cumberbatch et al., Animal Genetics, No. 37, pp. 393-396, 2006.
Krco et al, The Journal of Immunology, No. 156, pp. 2761-2768, 1996.
Batsalova et al. "Mice Producing Less Reactive Oxygen Species Are Relatively Resistant to Collagen Glycopeptide Vaccination against Arthritis" J. Immunol. (2010) 185;2701-2709.

* cited by examiner

*Primary Examiner* — G. R. Ewoldt
(74) *Attorney, Agent, or Firm* — Saffire IP; Daren P. Nicholson

(57) ABSTRACT

Novel complexes of peptides from human collagen type II and types of MHC class II associated with rheumatoid arthritis are provided. There is also provided novel therapies and methods for diagnosis of rheumatoid arthritis.

Figure 1:
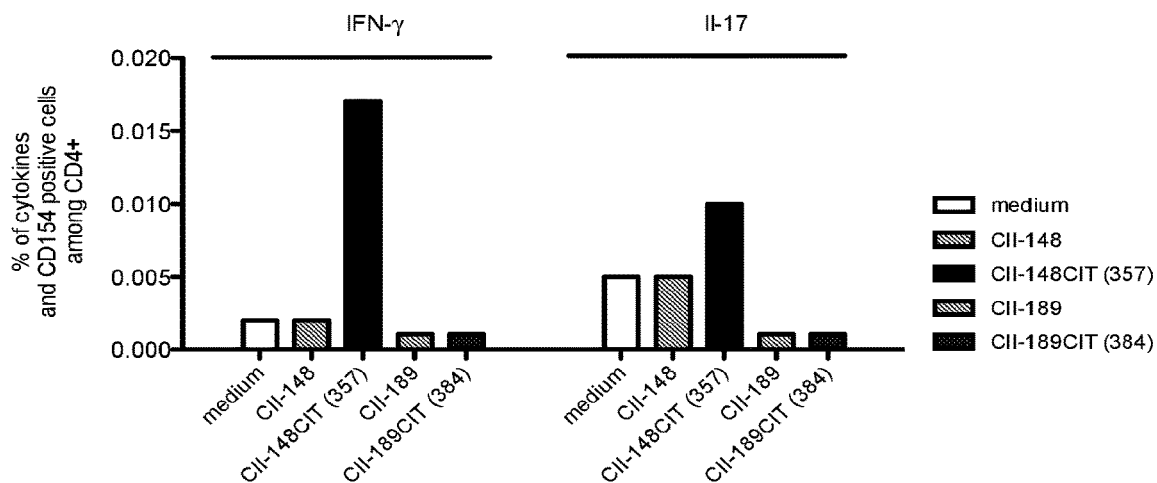
Figure 1:
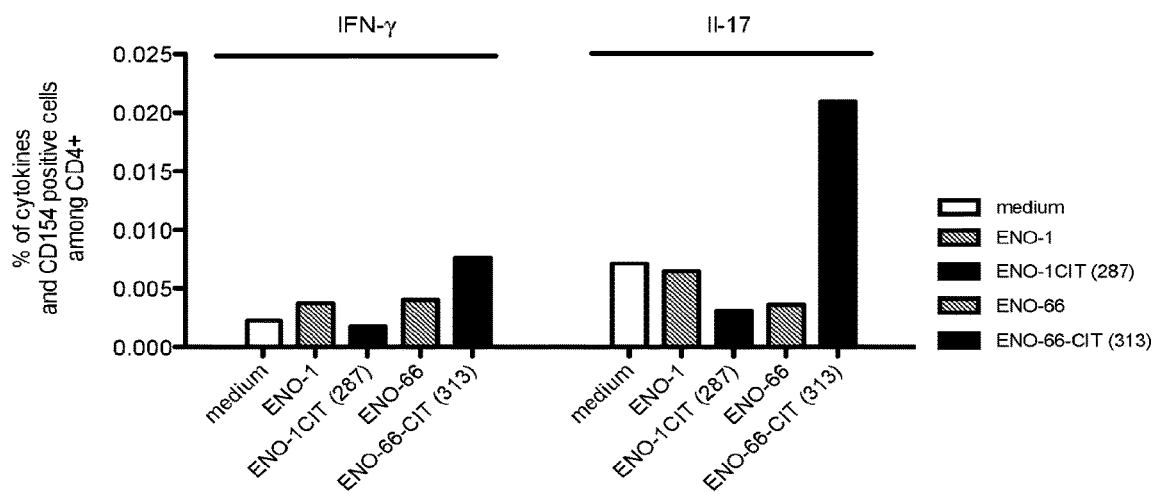

12 Claims, 3 Drawing Sheets
Specification includes a Sequence Listing.

COMPLEXES OF TYPES OF MHC CLASS II THAT BIND TO COLLAGEN TYPE II PEPTIDES AND THEIR USE ON DIAGNOSIS AND TREATMENT

CROSS-REFERENCE TO RELATED APPLICATIONS

This application is a continuation of U.S. patent application Ser. No. 14/009,886, with a filing or 371 (c) date of Mar. 25, 2014, which is a 35 U.S.C. § 371 National Phase Entry Application of International Application No. PCT/SE2012/050378 filed Apr. 5, 2012, which designates the U.S., and which claims benefit under 35 U.S.C. § 119(e) of U.S. Provisional Patent Application Ser. No. 61/472,122 filed on Apr. 5, 2011, and Swedish Application No. 1150297-8 filed on Apr. 5, 2011, the contents of each of which are incorporated herein by reference in their entireties.

The instant application contains a Sequence Listing, which has been submitted in text format via EFS-Web and is hereby incorporated by reference in its entirety. Said text copy, created on Apr. 9, 2018, is named 14953,484 Substitute_SL_9Apr2018.txt and is 20,276 bytes in size.

TECHNICAL FIELD

The present invention relates generally to novel peptides and their use in the treatment of rheumatoid arthritis and other forms of arthritis.

BACKGROUND ART

Autoimmune diseases are pathological conditions where an immune response is triggered by tissues and substances naturally present in the body. This unwanted and inappropriate immune reaction can be tissue-specific, organ-specific or systemic. The course of the disease proceeds from mild symptoms to irreversible destruction of specific tissues and/or organs.

Rheumatoid arthritis is a heterogeneous and partially genetically determined inflammatory disease, where autoimmunity is assumed to play an important pathogenic role, but where the specificity of the autoimmune reactions and the genetic determinants of these reactions remains incompletely known. It is a chronic and incurable disease that causes irreversible damage to the articular cartilage and bone, and which leads to progressive physical disability, The treatment and/or alleviation of rheumatoid arthritis, as well as other inflammatory and autoimmune diseases, have so far been based on the manipulation of immune and inflammatory events without knowing the detailed immunological basis of the disease. These therapies include traditional disease-modifying anti-rheumatic therapies (DMARD:s), including the administration of drugs such as methotrexate, sulfasalazine, azathioprine, leflunomide, hydroxychloroquine and cyclosporine. Methotrexate is often considered as the first choice medication. This drug is, however, associated with both milder and reversible side-effects, such as gastrointestinal and oral mucosal ulceration, but also with more serious, irreversible side effects, such as hepatic toxicity.

In addition to the DMARD:s, there are new protein-based therapies that affect cytokine regulation or broad aspects of T and B cell activation and migration. Examples are several monoclonal antibodies and a receptor construct that blocks TNF alpha, cytokine-blocking agents, such as antibodies against IL-6 receptor (tocilizumab), as well as therapies such as CTLA4Ig (abatacept) and anti-CD20 antibodies (rituximab) that influences entire classes of lymphocytes. Many novel therapies are not based on detailed knowledge of specificity of the autoimmune reactions in rheumatoid arthritis, but affect general signaling pathways. One such therapy is the Jak-2 inhibitor tofacitinib, currently in advanced clinical development. However, these novel therapeutics does still not address the specific autoimmune reaction but are non-specific treatments that affect large downstream parts of the immune and inflammation defense system, thereby giving rise to risks for side effects caused by a generally suppressed immune defense. Such side effects include sensitivity to infections and reduced response to vaccination.

Autoimmune reactions to certain epitopes of self antigens most likely contribute to the development of autoimmune diseases, such as rheumatoid arthritis. Antibodies against the patient's own proteins, in particular against native and/or post-translationally modified variants of certain proteins have been identified in patients with rheumatoid arthritis. Autoantibodies have been identified against collagen type II (the major protein in joint cartilage), alpha-enolase (an enzyme involved in glycolysis) and vimentin (an intermediate filament protein).

These antibodies are often—but not always—directed towards citrullinated variants of the proteins. Citrulline is an unconventional amino acid that results from the deimination of arginine. Citrullination of the arginine residue is a post-translational modification catalyzed by enzymes called peptidylarginine deiminases (PADs).

Previously, the use of citrullinated peptides as a diagnostic tool for rheumatoid arthritis (anti CCP) has been described (WO2003/050542). The CCP antibody assay uses a mixture of peptides that have not been demonstrated to occur as natural autoantigens (targets of B cells) in patients with rheumatoid arthritis.

Another reference, WO 2007/017556, describes the use of certain citrullinated and non-citrinullated peptides from collagen type II for the diagnosis of rheumatoid arthritis. Furthermore, the detection of a citrullinated enolase peptide (cep1) has been described as a diagnostic tool in rheumatoid arthritis (WO2008/090360). Citrullinated peptides from the protein vimentin have also been suggested for the diagnosis of rheumatoid arthritis (WO2007/123976).

However, these methods for diagnosis do not provide the whole picture of the disease in the individual since additional target molecules and mechanisms may be of importance for rheumatoid arthritis.

The available methods for diagnosis and treatment of autoimmune diseases clearly leave room for improvement. There is a need for a deeper insight into the pathogenesis of autoimmune diseases, as well as for the development of new diagnostic and therapeutic methods. With particular regard to rheumatoid arthritis, there is major unmet medical need for improved diagnosis and treatment. One problem in defining rheumatoid arthritis and its subsets has been the lack of a distinct clinical, laboratory or radiological marker for the disease and its subsets. Another problem resides in finding a reliable approach to both short-term and long-term monitoring of the progression or remission of the disease. A further problem resides in finding more specific and effective treatments, minimizing the side effects usually associated with both DMARD:s and currently available and currently developing therapies. These problems, and others evident to a skilled person upon study of the present description, will be addressed below.

3

Definitions

As used herein:

"Diagnosis": refers to determining with respect to an individual: whether the individual has a disease or not and/or how severe the disease of the individual is and/or prognosis of the disease of the individual and/or expected response to treatment of the individual and/or or risk of developing the disease, classification of the disease, monitoring the progression of the disease or the results of intervention.

"Patient" refers to an individual that have a disease or that have an increased risk of developing a disease. Thus, the disease may not necessarily have presented in the individual for the individual to be considered to be a patient. The increased risk can be detected by, for example, determining the genotype of the patient.

"Variant" of a peptide refers to a variant of a defined peptide comprising from between 8 and 20 amino acids, more preferably of between 9 and 19, even more preferably of between 13 and 18 amino acids and most preferably between 14 and 16 amino acids, comprising at least 8 consecutive amino acids, more preferably at least 10 consecutive amino acids, more preferably at least 12 consecutive amino acids, more preferably at least 13 consecutive amino acids, more preferably 14 consecutive amino acids is present in the defined peptide. The remaining residues of the peptide, if any, can be any naturally occurring amino acid.

"Sample" when used in relation to cells, refers to the original cells and also to the descendants of those cells, as cells may proliferate during in vitro culture.

"Enolase", as used herein, refers to the human alpha enolase protein.

"Amino acid", when used in the context of a peptide or a protein, refers to amino acid residue.

The immune response is controlled by T-cells where activating T-cells such as effector T-cells enhance the immune response and regulatory T-cells constitute one of several mechanisms that inhibit the immune response. Thus, autoimmune disease is controlled by a balance of stimulating effector T-cells and regulatory T-cells. Effector T-cells and regulatory T-cells both belong to the class of T-helper cells. Activated effector T-cells secrete various pro-inflammatory cytokines such as interferon gamma, TNF alpha and IL-17 that contributes to inflammation.

The human leukocyte antigen (HLA) loci encodes the genes for human MHC class II proteins (referred to herein as "MHC" or "MHC protein"), which plays a crucial role in regulation of the immune system. Display of immunogenic peptides by MHC class II molecules on the surface of antigen-presenting cells serve as signals to T-cells which in turn control the immune reaction and also progression of the autoimmune disease by inducing proliferation of B-cells and production of pathological antibodies. A crucial step of T-cell activation is the binding of the T-cell receptor of the T-cell to a complex consisting of an antigenic peptide bound to the cleft of a MHC class II protein molecule on the surface of an antigen-presenting cell.

The MHC protein system is adapted to bind and exhibit diverse peptides to T-cells. This is usually beneficial since many different peptides, for example from pathogens, thereby can be detected by the immune system.

HLA genotypes are well known and have been described previously. The beta-subunit of the MHC protein is the subunit that contributes most to the diversity of MHC. In fact, the HLA-DRB1 locus on chromosome 6 that encodes this subunit is among the most diverse in man. Most differences are located in the peptide-binding cleft of the MHC protein.

4

SUMMARY OF INVENTION

Previously, treatment as well as diagnosis of rheumatoid arthritis has been carried out without regard to the genetic predisposition of the patient of to the fine specificity of the autoimmune reactions typical for rheumatoid arthritis. Now, the inventors disclose methods of diagnosis and treatment of rheumatoid arthritis heralds the era of personalized medicine in rheumatoid arthritis. By using the inventive peptides together with information of the genotype of the patient, the particular immune response of the individual patient can be analyzed, monitored and treated. In particular the role of antigen presentation to T-cells in patients can be determined and monitored by using the diagnostic reagents and methods described herein.

The inventors make available novel peptides and their uses in diagnosis, alleviation and treatment of rheumatoid arthritis and other forms of arthritis, such as osteoarthritis, psoriasis arthritis, spondyloarthropathies or relapsing polychndritis.

Figure 2:
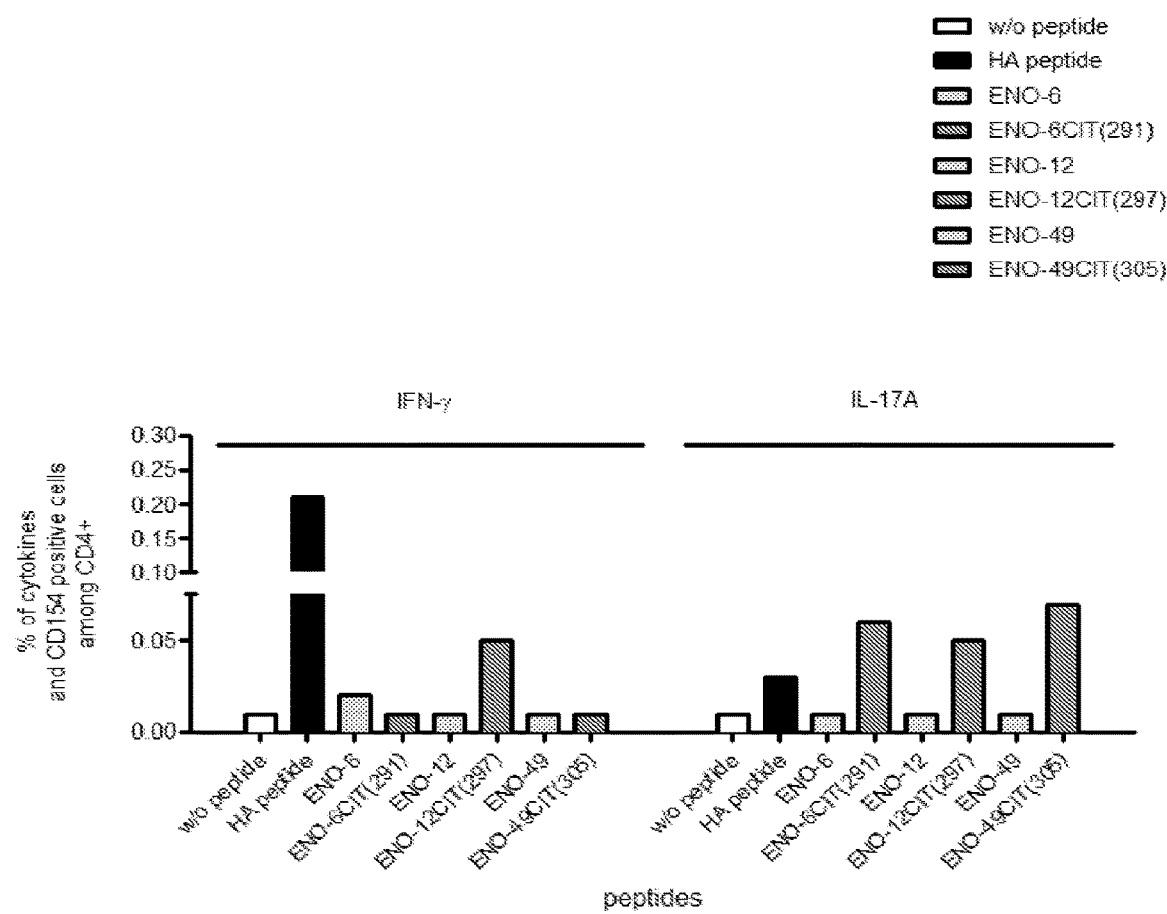
Figure 3:
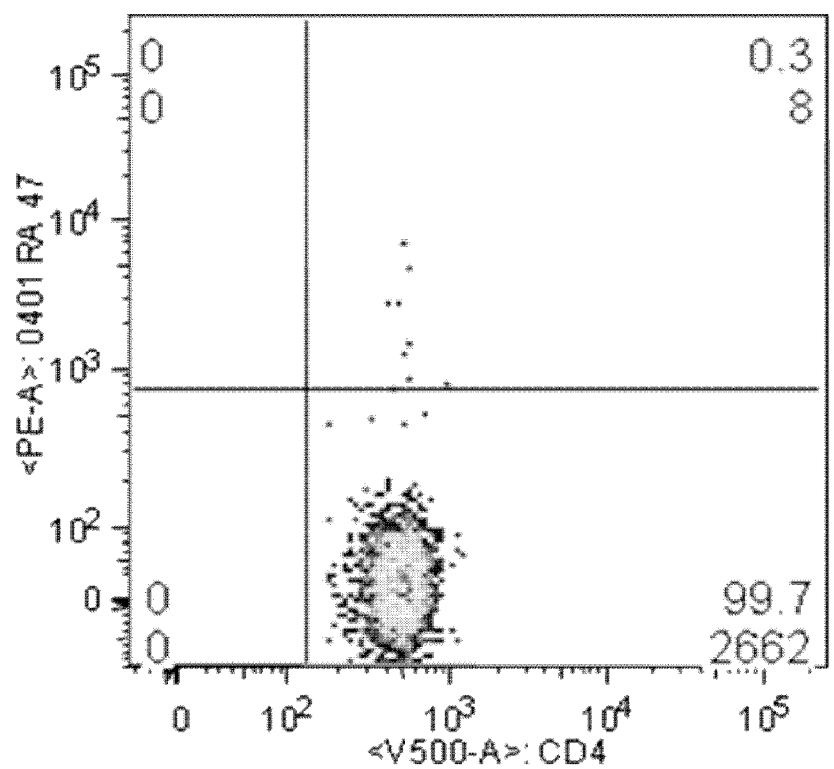

FIGS. 1-3 provide data from experiments using the peptides and are discussed more thoroughly below and in the Examples section.

One object of the present invention is to provide novel therapies for particular rheumatoid arthritis and other forms of arthritis, such as osteoarthritis, psoriasis arthritis, spondyloarthropathies or relapsing polychndritis, in particular for patients with the MHC class II genotypes HLA-DRB1 0101, HLA-DRB1 0404, HLA-DRB1 0401, HLA-DRB1 0405, HLA-DRB1 0408 and HLA-DRB1 1001.

Another objective of the present invention is to provide novel methods for diagnosis of rheumatoid arthritis.

Therefore it is provided a peptide of between 8 and 20 amino acids comprising at least 8 consecutive amino acids residues with a sequence present in one of SEQ ID NO 1, 2, 3, 4, 5, 6, 7, 8, 10, 11, 12, 13, 15, 16, 17, 18, 19, 20, 21, 22, 23, 24, 25, 26, 27, 30, 31, 32, 34, 35, 36, 38, 39, 40, 41, 43, 45, 46, 47, 48, 49, 50, 51, 52, 53, 54, 55, 56, 57, 58, 60, 61, 62, 63, 64, 65, 66, 67, 69, 72, 73, 74, 75, 78, 79, 80, 81, 82, 83, 84, 85, 86 and 87.

The peptide can also essentially consist or consist of a sequence selected from SEQ ID NO 1, 2, 3, 4, 5, 6, 7, 8, 10, 11, 12, 13, 15, 16, 17, 18, 19, 20, 21, 22, 23, 24, 25, 26, 27, 30, 31, 32, 34, 35, 36, 38, 39, 40, 41, 43, 45, 46, 47, 48, 49, 50, 51, 52, 53, 54, 55, 56, 57, 58, 60, 61, 62, 63, 64, 65, 66, 67, 69, 72, 73, 74, 75, 78, 79, 80, 81, 82, 83, 84, 85, 86 and 87.

In particular SEQ ID NO 11, 15, 16, 17, 18, 19, 20, 21, 22, 23, 24 and 34 are suitable.

The peptide may be a peptide with SEQ ID NO 15, 16, 17, 18, 19, 20, 21, 22, 23, 24, 30, 31, 36, 45, 46, 47, 48 and SEQ ID NO 72, 73, 74, 75, 78, 79, 80, 81, 82, 83, 84, 85, 86 and 87 and where said peptide comprises at least one citrulline residue.

The peptide may be an enolase peptide such as one of SEQ ID NO 1, 2, 3, 4, 5, 6, 7, 8, 10, 11, 12, 13, 15, 16, 17, 18, 19, 20, 21, 22, 23 24, 32, 34, 35 and 36.

The peptide may be a citrinullated enolase peptide such as one of SEQ ID NO 15, 16, 17, 18, 19, 20, 21, 22, 23, and 36, said peptide comprising at least one citrulline residue.

The peptide may have sequence selected from the collagen type II sequences SEQ ID NO 25, 26, 27, 30, 31, 38, 39, 40, 41, 43, 45, 46, 47 and 48.

The peptide may consist of a citrinullated sequence selected from the collagen type II sequences SEQ ID NO 30, 31, 45, 46, 47 and 48, said peptide comprising at least one citrulline residue.

The peptide can have a sequence selected from SEQ ID NO 49, 50, 51, 52, 53, 54, 55, 56, 57, 58, 60, 61, 62, 63, 64, 65, 66, 67, 69, 72, 73, 74, 75, 78, 79, 80, 81, 82, 83, 84, 85, 86 and 87.

The peptide may consist of a sequence is selected from SEQ ID NO 72, 73, 74, 75, 78, 79, 80, 81, 82, 83, 84, 85, 86, and 87, said peptide comprising at least one citrulline residue.

It is also provided a peptide or peptide-MHC complex according to the invention for use in diagnosis of rheumatoid arthritis or other types of arthritis Also, a method for diagnosis of rheumatoid arthritis or other types of arthritis is provided. In its most general form, the method comprises the steps of: 1) obtaining a sample of T-cells from a patient, 2) contacting the sample comprising T-cells with a peptide or a peptide-MHC complex according to the invention, 3) detecting the ability of the T-cells to become activated by the peptide or peptide-MHC complexes. This third step can be carried out by detecting a marker in the sample of T-cells, or detecting binding of the peptide or peptide-MHC complex to the T-cells. Both these steps can be carried out.

There is also provided a kit of parts intended for use in diagnosis, the kit comprising a peptide peptide-MHC complex according to the invention. The kit can comprise at least one cell culture vessel. Furthermore, the kit can provide means for detecting the expression of at least one protein selected from the group consisting of CD3, CD4, Foxp3, CD25, TNF alpha, Interferon gamma, IL-17A, IL-17F, CD154, CD69, Ki 67, IL-2, IL-10 and IL-10. In particular, CD4, CD154, IL-17A, IL-17F, interferon gamma and TNF alpha are suitable. The means for detecting the expression of a protein can be an antibody against said protein or a set primers for RT-PCR (real-time PCR).

Furthermore it is provided the use of a peptide of between 8 and 20 amino acids comprising at least 8 consecutive amino acid residues with a sequence present in a sequence selected from SEQ ID NO 1, 2, 3, 4, 5, 6, 7, 8, 9, 10, 11, 12, 13, 14, 15, 16, 17, 18, 19, 20, 21, 22, 23, 24, 25, 26, 27, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86 and 87, or a complex of such a peptide and a human recombinant MHC class II protein, for the treatment of rheumatoid arthritis or other types of arthritis. In particular the peptide may consists of a sequence selected from one of SEQ ID NO 1, 2, 3, 4, 5, 6, 7, 8, 9, 10, 11, 12, 13, 14, 15, 16, 17, 18, 19, 20, 21, 22, 23, 24, 25, 26, 27, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86 and 87. These peptides and variants of these peptides, and peptide-MHC complexes are also suitable for use in the method of diagnosis described above and for inclusion in the kit as described above. There is also provided a complex of a peptide according to the invention and a human recombinant MHC class II protein (peptide-MHC complex), and such a complex for use in the treatment of rheumatoid arthritis or other types of arthritis. Furthermore, there is provided a method for treatment of rheumatoid arthritis comprising administering such a peptide or peptide-MHC complex according to the invention to a patient. There is also provided a pharmaceutical composition comprising these peptide or peptide-MHC and the use of these peptides and peptide-MHC complexes for the manufacture of a therapeutic.

DETAILED DESCRIPTION

The invention concerns novel peptides and the use of these peptides from human alpha-enolase (SEQ ID NO 1 to SEQ ID NO 13, SEQ ID NO 15 to SEQ ID NO 24 and SEQ ID NO 32 to SEQ ID NO 36 and SEQ ID NO 14) human collagen type II (SEQ ID NO 25, 26, 27, 30 and 31 and SEQ ID NO 37 to SEQ ID NO 48), and human vimentin (SEQ ID NO 49 to SEQ ID NO 87) that binds to the human MHC class II protein associated with rheumatoid arthritis, in particular MHC class II of the genotypes HLA-DRB10401, 0404, 0405, 0408, 0101 and 1001.

The peptides are able to bind with a high affinity to the MHC protein such that they will not easily disengage from the MHC protein once bound. The affinity is higher than the affinity of the CLIP peptide for the MHC protein (the CLIP peptide is the part of the invariant chain of the MHC protein that binds to the peptide-binding groove of the MHC protein during MHC protein assembly). The off-rate of the peptide is sufficient so that peptide-loaded MHC can stimulate T-cells in vitro, even after several days of incubation in peptide-free media. The binding of the CLIP peptide to the MHC class II molecule compared to the binding of the peptide can be determined in inhibition assays and also by the presentation of the relevant peptides after feeding antigen presenting cells with the full protein. An acceptable off-rate can be determined by methods known to a person skilled in the art, for example by using gel filtration assays. The peptides bind in the antigen presenting cleft of the MHC protein, such that the peptide-MHC-complex can be recognized and bind to a T-cell receptor or another protein specific for the peptide or for the peptide-MHC complex. Preferably the peptide thus bound to the T-cell receptor is able to provide a signal to the T-cell that activates the T-cell.

It is provided, in a first aspect of the invention, a peptide of between 8 and 20 amino acids, more preferably of between 9 and 19, even more preferably of between 13 and 18 amino acids, and most preferably 14 to 16 amino acids, comprising at least 8 consecutive amino acids, more preferably at least 10 consecutive amino acids, more preferably at least 12 consecutive amino acids, more preferably at least 13 consecutive amino acids, more preferably 14 consecutive amino acids and most preferably 15 consecutive amino acids residues with a sequence present in a sequence selected from SEQ ID NO 1 to SEQ ID NO 13 (SEQ ID NO 1, 2, 3, 4, 5, 6, 7, 8, 9, 10, 11, 12 and 13); SEQ ID NO 15 to 27 (SEQ ID NO 15, 16, 17, 18, 19, 20, 21, 22, 23, 24, 25, 26 and 27); and SEQ ID NO 30 to SEQ ID NO 87 (SEQ ID NO 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86 and 87), in particular SEQ ID NO 11, 15, 16, 17, 18, 19, 20, 21, 22, 23, 24, 34 and 46.

A peptide shorter than 8 amino acids or longer than 20 amino acids does not bind well to the MHC protein. Between eight and fifteen consecutive amino acids of the peptide should have a sequence present in one of SEQ ID NO 1 to SEQ ID NO 13, SEQ ID NO 14, SEQ ID NO 15 to SEQ ID NO 27 and SEQ ID NO 30 to SEQ ID NO 87. The remaining residues of the peptide, if any, can be any naturally occurring amino acid, provided that the peptide binds to the MHC protein and is able to induce binding of a T-cell receptor and is able to provide a signal to the T-cell that activates the T-cell as described herein.

The peptide may consist of a sequence selected from SEQ ID NO 1 to SEQ ID NO 13 (SEQ ID NO 1, 2, 3, 4, 5, 6, 7, 8, 9, 10, 11, 12 and 13); SEQ ID NO 15 to 27 (SEQ ID NO 15, 16, 17, 18, 19, 20, 21, 22, 23, 24, 25, 26 and 27) and SEQ ID NO 30 to SEQ ID NO 87 (SEQ ID NO 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86 and 87), in particular SEQ ID NO 11, 15, 16, 17, 18, 19, 20, 21, 22, 23, 24, 34 and 46. The peptide may, alternatively, consist of the sequence in SEQ ID NO 14.

In particular the citrinullated peptides with SEQ ID NO 14, 15, 16, 17, 18, 19, 20, 21, 22, 23, 24 and the non-citrinullated peptides 11 and 34, or a variant of such a peptide, are suitable.

Some of the suitable peptides are citrullinated, such as peptides and variants of peptides comprising a sequence as defined in SEQ ID NO 14 and SEQ ID NO 15 to SEQ ID NO 24 (SEQ ID NO 15, 16, 17, 18, 19, 20, 21, 22, 23 and 24) and SEQ ID NO 30, 31, 36, 45, 46, 47, 48 and SEQ ID NO 71 to SEQ ID NO 87 (SEQ ID NO 71, 72, 73, 74, 75, 76, 77, 78, 79, 80, 81, 82, 83, 84, 85, 86 and 87) and where the peptide comprises at least one citrulline residue. SEQ ID NO 14 and SEQ ID NO 15 to SEQ ID NO 24 (SEQ ID NO 15, 16, 17, 18, 19, 20, 21, 22, 23 and 24) and SEQ ID NO 36 are citrullinated alpha-enolase peptides, SEQ ID NO 30, 31, 45, 46, 47 and 48 are citrullinated collagen type II peptides and SEQ ID NO 71 to SEQ ID 87 (SEQ ID NO 71, 72, 73, 74, 75, 76, 77, 78, 79, 80, 81, 82, 83, 84, 85, 86 and 87) are citrullinated vimentin peptides. One advantage with using citrullinated peptides is that they may be more efficient and specific in the treatment of rheumatoid arthritis as the autoantibodies that cause rheumatoid arthritis are often directed towards peptides containing a citrulline residue. Furthermore, citrullinated peptides often bind better to the MHC protein than the corresponding arginine peptide, as described in the present invention.

The inventive peptides are able to bind to the MHC class II protein in vivo or in vitro.

The peptides according to the invention can be obtained pure and in large quantities by means of organic synthesis, such as solid phase synthesis. Methods for peptide synthesis are well known to a person to skilled in the art. For example, R. B. Merrifield (1963). J. Am. Chem. Soc. 85 (14): 2149-2154, Merrifield (1990) Int. J. Peptide. Protein Res 35: 161-214, Atherton E. et al (1979) Bioorg Chem. 8, 351, US2009/0292108 and 2009/0221792 and references therein describes peptide synthesis. In addition the peptides may be synthesized using an automatic peptide synthesis machine. Of course, the peptides may easily be obtained from a commercial supplier of peptides. In addition, peptides that do not comprise a citrulline residue can be produced using recombinant DNA technology.

The peptides can be linear or circular. A circular peptide may be suitable for certain applications, such as when the peptide is used for detecting a pathogenic antibody, for example in an ELISA assay. A circular peptide is less suitable for binding to a MHC protein or for assays for T-cell activation.

In another aspect of the invention it is provided a complex, as described above, of a peptide according to the invention and human recombinant MHC class II protein, in particular one of the MHC class II variants HLA-DRB1 0401, 0404, 0405, 0408, 0101 or 1001 that bind to such a peptide ("peptide-MHC complex"). The MHC protein need not be the full length protein. A fragment of a MHC protein can also be used, as discussed below. Herein, "peptide-MHC complex" refers also to a complex of a peptide and such a fragment of a MHC class II protein.

Preferred combinations of MHC class II protein and peptides are as follows:

MHC class II with genotype HLA-DRB1 0401 bound to a peptide with a sequence selected from SEQ ID NO 7, 8, 9, 10 and 11, 14, 15, 16, 17, 18, 19, 20, 21, 22, 23, 24, 25, 26, 30, 31, 33, 34, 36, 45, 49, 50, 54, 55, 58, 59, 60, 61, 63, 64, 65, 66, 69, 71, 72, 73, 74, 75, 76, 77, 78, 79, 82, 83, 84 and 86, or a variant of such a peptide. In particular the citrullinated peptides and variants of these in that group are suitable, that is SEQ ID NO 14, 15, 16, 17, 18, 19, 20, 21, 22, 23, 24, 30, 31, 36, 45, 71, 72, 73, 74, 75, 76, 77, 78, 79, 82, 83, 84 and 86. Most preferred peptides for MHC class II protein with a 0401 genotype are peptides with SEQ ID NO 11, 14, 15, 16, 17, 18, 19, 20, 21, 22, 23, 24 and 34, or variants thereof.

MHC class II with genotype HLA-DRB1 0404 bound to a peptide with a sequence selected from SEQ ID NO 1, 2, 4, 5, 6, 7, 8, 10, 11, 14, 13, 16, 17, 20, 21, 23, 24, 25, 26, 27, 30, 31, 33, 34, 37, 38, 40, 41, 45, 49, 50, 53, 57, 58, 60, 62, 68, 70, 71, 75, 77 and 87, or a variant of such a peptide. In particular the citrullinated peptides and variants of these in that group are suitable, that is SEQ ID NO 14, 16, 17, 20, 21, 23, 24, 30, 31, 45, 71, 75, 77 and 87.

MHC class II with genotype HLA-DRB1 0405 bound to a peptide with a sequence selected from SEQ ID NO 1, 2, 3, 7, 8, 9, 10, 11, 12, 14, 15, 16, 17, 18, 19, 20, 21, 22, 23, 24, 26, 31, 32, 33, 34, 35, 36, 39, 41, 44, 45, 50, 60, 65, 67, 73 and 77, or a variant of such a peptide. In particular the citrullinated peptides and variants of these in that group are suitable, that is, SEQ ID NO 14, 15, 16, 17, 18, 19, 20, 21, 22, 23, 24, 31, 36, 45, 73 and 77.

MHC class II with genotype HLA-DRB1 0408 bound to a peptide with a sequence selected from SEQ ID NO 3, 5, 6, 7, 9, 10, 11, 12, 33, 34, 36 and 48, or a variant of such a peptide. In particular the citrullinated peptides and variants of these in that group are suitable, that is, SEQ ID NO 36 and 48.

MHC class II with genotype HLA-DRB1 0101 bound to a peptide with a sequence selected from SEQ ID NO 1 to SEQ ID NO 13, (SEQ ID NO 1, 2, 3, 4, 5, 6, 7, 8, 9, 10, 11, 12 and 13), SEQ ID NO 14, SEQ ID NO 16, 17, 23, 26, 32, 33, 49, 50, 52, 56, 57, 61, 63, 65, 67, 68, 72, 74, 75, 76, 77, 79, 80, 81 and 85, or a variant of such a peptide. In particular the citrullinated peptides and variants of these in that group are suitable, that is, SEQ ID NO 14, 16, 17, 23, 72, 74, 75, 76, 77, 79, 80, 81, and 85.

MHC class II with genotype HLA-DRB1 1001 bound to a peptide with a sequence selected from SEQ ID NO 1, 3, 10, 14, 16, 42, 43, 46, 47 and 48, or a variant of such a peptide. In particular the citrullinated peptides and variants of these in that group are suitable, that is, SEQ ID NO 14, 16, 46, 47 and 48. In particular a peptide with SEQ NO 46 or a variant thereof, is suitable.

The peptide-MHC complex can be produced by methods known in the art. Recombinant expression of MHC protein and the loading of the MHC protein with a peptide are well known to a person skilled in the art. One suitable expression system for the production of MHC protein is baculovirus.

As mentioned, the fragment of a MHC protein can be used. The MHC protein should be stable and be able to present a peptide to T-cells. For use as described herein, the essential part of the MHC class II molecule are the outer domains of the alpha and the beta chains (alpha 1 and beta 1 domains) that together form the peptide binding cleft. For example, it may be suitable to exclude the transmembrane domains from such a fragment, order to achieve solubility of the recombinant protein. In order to obtain a functional MHC protein that binds and presents a peptide, the outer domains (alpha1 and beta1) can be stabilized by different means. Such means include the following strategies: a) retaining parts of the inner domains (alpha 2 and beta 2 domains), b) stabilizing the inner domains by the introduction of a leucine zipper structure, c) introducing cysteine residues that form disulfide bridges that links the alpha and the beta chains, d) introducing a peptide in the peptide binding groove that is covalently linked to an elongation of the beta-domain. Suitable genes encoding MHC protein are DRB1 for the beta chain and DRA for the alpha chain. Molecular biology methods known to a person skilled in the art can be used to alter these genes. Useful protocols can be found in Molecular Cloning: A Laboratory Manual, Third Edition by Joe Sambrook.

The following references are relevant for the production of recombinant MHC protein: 1) Novak E J, Liu A W, Nepom G T, Kwok W W MHC class II tetramers identify peptide-specific human CD4+ T cells proliferating in response to influenza A antigen. J Clin Invest 1999; 104: R63-7; 2) Dzhambazov, B., et al. Therapeutic Vaccination of Active Arthritis with a Glycosylated Collagen Type II Peptide in Complex with MHC Class II Molecules. J Immunol 176, 1525-1533 (2006); 3) Smith, K. J., Pyrdol, J., Gauthier, L., Wiley, D. C. & Wucherpfennig, K. W. Crystal structure of HLA-DR2 (DRA*0101, DRB1*1501) complexed with a peptide from human myelin basic protein. J Exp Med 188, 1511-1520 (1998); 4) Andersson, E. C., et al. Definition of MHC and T cell receptor contacts in the HLA-DR4 restricted immunodominant epitope in type II collagen and characterization of collagen-induced arthritis in HLA-DR4 and human CD4 transgenic mice. Proc Natl Acad Sci USA 95, 7574-7579 (1998); 5.) Svendsen, P., et al. Tracking of proinflammatory collagen-specific T cells in early and late collagen-induced arthritis in humanized mice. J Immunol 173, 7037-7045 (2004).

Binding of the peptide to the MHC class II protein so that they form a complex can be carried out in different manners. Often it is sufficient to incubate the MHC protein for a certain time for the peptide to bind to the protein. Usually incubation is to be carried out for several days, in particular 3 days is a suitable time for incubation. The peptide can be present in a molar excess to the MHC protein. A suitable molar excess of peptide is 20 times. A suitable concentration of peptide is 0.2 mg/ml.

The MHC protein consists of an alpha chain and a beta chain. The alpha/beta complex of the MHC protein may be unstable in solution unless a peptide is bound to the protein. It may therefore be suitable to store the MHC protein with a non-specific "dummy peptide" bound to the peptide binding-cleft in order to improve stability. Before use, the non-specific peptide is removed and replaced with the peptide of interest. It may also be suitable to crosslink the peptide to the MHC class II protein.

The peptides according to the invention are suitable for use in the treatment and diagnosis of rheumatoid arthritis.

As discussed above, the immune response is controlled by T-cells where regulatory T-cells constitutes one of several mechanisms that inhibit the immune response and where activating effector T-cells enhance the immune response. Thus, autoimmune disease, such as rheumatoid arthritis, is controlled by a balance of stimulating effector T-cells and regulatory T-cells.

A pathological immune response can be attenuated by administering the peptides or peptide-MHC complexes so that the regulatory T-cells or other regulatory pathways are specifically stimulated. The stimulation with soluble peptide-MHC complexes can be carried out without the presence of co-stimulatory factors normally present on the surface of antigen presenting cells such as B7 surface molecules. The purpose of this is to activate regulatory T cells, rather than effector T-cells which are disease-promoting. The regulatory T-cell then inhibits pathological inflammatory cell, T cell, or B-cell activation and antibody production.

The peptide can be provided or administered in a form where it is bound to a MHC protein, in particular a recombinant human MHC class II protein (peptide-MHC complex). An advantage with providing or administering the peptide together with a MHC class protein is that this may facilitate reactivity with T-cells and provide a more efficient tolerization than use of the peptide alone. This complex may also provide a more suitable drug as it has a longer half-life in the human body. Preferably, a MHC class II protein with a genotype that corresponds to the genotype of the patient is administered to the patient.

Thus, by administering one or more of the inventive peptides or peptide-MHC complexes to patients with an autoimmune disease such as rheumatoid arthritis, the immune system can be modulated and the disease can be prevented, cured, controlled or at least attenuated.

Patients are suitably treated according to the nature of their autoimmune response and their genotype. HLA genotypes are well known and have been described previously. Patients that carry at least one allele of HLA-DRB1 0101, HLA-DRB1 0404, HLA-DRB1 0401, HLA-DRB1 0405, HLA-DRB1 0408 and HLA-DRB1 1001 are of interest for diagnosis and/or treatment using the disclosed peptides. However, it is possible that patients with other genotypes are of interest also.

Patients that carry the HLA genotype HLA-DRB1 0101 are advantageously treated with at least one peptide with a sequence selected from SEQ ID NO 1 to SEQ ID NO 13, (SEQ ID NO 1, 2, 3, 4, 5, 6, 7, 8, 9, 10, 11, 12 and 13) SEQ ID NO 14, SEQ ID NO 16, 17, 23, 26, 32, 33, 49, 50, 52, 56, 57, 61, 63, 65, 67, 68, 72, 74, 75, 76, 77, 79, 80, 81 and 85, or a variant of such a peptide. In particular the citrullinated peptides and variants of these in that group are suitable, that is SEQ ID NO 14, 16, 17, 23, 72, 74, 75, 76, 77, 79, 80, 81, and 85.

Patients that carry the HLA genotype HLA-DRB1 0401 are advantageously treated with at least one peptide with a sequence selected from SEQ ID NO 7, 8, 9, 10 and 11, 14, 15, 16, 17, 18, 19, 20, 21, 22, 23, 24, 25, 26, 30, 31, 33, 34, 36, 45, 49, 50, 54, 55, 58, 59, 60, 61, 63, 64, 65, 66, 69, 71, 72, 73, 74, 75, 76, 77, 78, 79, 82, 83, 84 and 86, or a variant of such a peptide. Alternatively a peptide with the sequence of SEQ ID NO 14 can be used, or a variant of such a peptide. In particular the citrullinated peptides and variants of these in that group are suitable, that is SEQ ID NO 14, 15, 16, 17, 18, 19, 20, 21, 22, 23, 24, 30, 31, 36, 45, 71, 72, 73, 74, 75, 76, 77, 78, 79, 82, 83, 84 and 86. In particular, the citrinullated peptides with SEQ ID NO 14, 15, 16, 17, 18, 19, 20, 21, 22, 23, 24 and the non-citrinullated peptides 11 and 34, or a variant of such a peptide, are suitable Patients that carry HLA genotype HLA-DRB1 0404 are advantageously treated with at least one peptide with a sequence selected from SEQ ID NO 1, 2, 4, 5, 6, 7, 8, 10, 11, 13, 14, 16, 17, 20, 21, 23, 24, 25, 26, 27, 30, 31, 33, 34, 37, 38, 40, 41, 45, 49, 50, 53, 57, 58, 60, 62, 68, 70, 71, 75, 77 and 87, or a variant of such a peptide. In particular the citrullinated peptides and variants of these in that group are suitable, that is SEQ ID NO 14, 16, 17, 20, 21, 23, 24, 30, 31, 45, 71, 75, 77 and 87.

Patients that carry HLA genotype HLA-DRB1 0405 are advantageously treated with at least one peptide with a sequence selected from SEQ ID NO 1, 2, 3, 7, 8, 9, 10, 11, 12, 14, 15, 16, 17, 18, 19, 20, 21, 22, 23, 24, 26, 31, 32, 33, 34, 35, 36, 39, 41, 44, 45, 50, 60, 65, 67, 73 and 77, or a variant of such a peptide. In particular the citrullinated peptides and variants of these in that group are suitable, that is SEQ ID NO 14, 15, 16, 17, 18, 19, 20, 21, 22, 23, 24, 31, 36, 45, 73 and 77.

Patients that carry HLA genotype HLA-DRB1 0408 are advantageously treated with at least one peptide with a sequence selected from SEQ ID NO 3, 5, 6, 7, 9, 10, 11, 12, 33, 34, 36 and 48, or a variant of such a peptide. In particular the citrullinated peptides and variants of these in that group are suitable, that is SEQ ID NO 36 and 48.

Patients that carry HLA genotype HLA-DRB1 1001 are advantageously treated with at least one peptide with a sequence selected from SEQ ID NO 1, 3, 10, 14, 16, 42, 43, 46, 47 and 48, or a variant of such a peptide. In particular the citrullinated peptides and variants of these in that group are suitable, that is SEQ ID NO 14, 16, 46, 47 and 48. A peptide with SEQ ID NO 46 or a variant thereof is the most preferred peptide.

Patients with an immune response against enolase are suitably treated with an alpha-enolase peptide according to the invention, preferably a peptide that corresponds to the epitope to which the autoimmunity is directed. However, also other patients with rheumatoid arthritis may be suitable for treatment with these peptides.

Patients with an immune response against collagen type II are suitably treated with a collagen type II peptide according to the invention, preferably a peptide that corresponds to the epitope to which the autoimmunity is directed. However, also other patients with rheumatoid arthritis may be suitable for treatment with these peptides.

Patients with an autoimmune response against vimentin are suitably treated with a vimentin peptide according to the invention. However, also other patients with rheumatoid arthritis may be suitable for treatment with these peptides.

The peptide or peptide-MHC complexes can be administered to the patient using different methods. Tolerating protocols are known and reviewed in Larché and Wraith, Peptide-based therapeutic vaccines for allergic and autoimmune disease. Nature Medicine Supplement; 2005; 11; 4; S69-S76. Examples of treatment protocols are described in Ludvigsson et al, GAD N Engl J Med. 2008 Oct. 30; 359(18):1909-20; Tisch et al, J Immunol. 2009; 183; 4809-4816); Vestberg et al, J Immunol. 2006; 176; 1525-1533); Shah et al, Journal of Internal Medicine 2009: 266, 221-23 Gianfrani et al, J Immunol. 2009; 182; 4158-4166). Thus, the peptide or peptide-MHC complexes can be used as a vaccine. Alternatively, the peptides can be linked to tolerogenic dendritric cells.

The vaccines can be administered either intravenously, intradermally, in the gut or via the airways (mucosal administration). Dosing is to be adjusted after monitoring the effects on specific immune responses of the patients (see below). The vaccine is initially administered to the patient 1, 2, 3 or 4 times, more preferably 2, 3 or 4 times. However it can also be administered repeatedly over several years of disease.

The peptide or peptide-MHC complex is administered to the patient in an effective and non-toxic amount. These parameters can be monitored using previously known clinical and immunological methods. In particular the efficacy of the vaccination can be monitored in patients using the diagnostic methods described herein (see below).

In yet another aspect of the invention it is provided a pharmaceutical composition comprising a peptide according to the invention or a complex of a peptide according to the invention and a human recombinant MHC class II protein (peptide-MHC complex). The pharmaceutical composition may comprise suitable additives such as enhancers of bioavailability, preservatives, solubility enhancers, adjuvants and stabilizers. In particular, the pharmaceutical composition may comprise an immunologic adjuvant, such as an aluminum salt. The pharmaceutical composition can include a micelle component for delivery of the peptide.

The peptides and peptide-MHC complexes can be used in diagnosis of rheumatoid arthritis. The immune response which causes rheumatoid arthritis is controlled by a balance of regulatory T-cells (characterized by the expression of CD4, CD25, and Foxp3) and stimulating effector T-cells (characterized by expression and of proinflammatory cytokines such as IFN gamma, TNF or IL-17A and IL-17F and surface expression of CD154 and CD69) where a change in the balance towards fewer or less active regulatory T-cells or other regulatory mechanisms leads to a continued or enhanced immune response and advancement of the disease. The disclosed peptides and peptide-MHC complexes can be used for monitoring the amount of T-cells that are reactive for autoimmune epitopes. In particular the relationship between the amount of regulatory T-cells and the amount of effector T-cells can be determined, where an increase of the proportion of effector T-cells, in particular activated effector T-cells, indicates advancement of the disease.

In this manner, the disease of the patient, and the profile of the T-cells that cause the diseases, can be monitored in the patient. This can be carried out at various time points in order to follow the progression of the disease in the patient. The peptides and peptide-MHC complexes can also be used to monitor the immune response during various interventions such as vaccination, or other therapy.

The assay can suitable be used for analysis of T-cells of a patient. Suitably the following steps are then carried out: 1) obtaining a sample of T-cells from a patient, 2) contacting the sample comprising T-cells with a peptide or a peptide-MHC complex according to the invention and 3) detecting the ability of the T-cells to become activated by the peptide or peptide-MHC complexes. This third step can be carried out by detecting a marker in the sample of T-cells or detecting binding of the peptide or peptide-MHC complex to the T-cells.

The detection of markers can serve the purpose of classifying the T-helper cells into of four groups: resting regulatory T-cells, activated regulatory T-cells, resting (naïve) effector T-cells and activated effector T-cells. Suitably markers that indicate activation the nature and activation state (active/inactive) of the T-cells are detected. The amount of cells and the ratio of these cell types to each other can also be quantified.

Detecting only binding of the peptide or peptide-MHC complex—without necessarily detecting the subsequent activation of T-cells—serves the purpose of detecting T-cells that bind to and thus is able to react with, and become activated by, the peptide or peptide-MHC complex in question. One advantage with this method is that no incubation time is necessary.

The method can include analysis of the cells themselves or a part or the cell culture media. Thus the "sample of T-cells" referred to above includes the cells themselves and any cell culture media used. Cell culture media is usually necessary if the cells are to survive in culture more than a few hours.

It can be suitable to contact the sample comprising T-cells under conditions that allow activation of the T-cells. The sample of T-cells suitably comprises T-helper cells. T-helper cells are characterized by the surface expression of CD4.

T-cells are contacted with the peptide or peptide-MHC complexes under conditions that allow activation of the T-cells, such as, for example, under appropriate cell cultivation conditions. Suitably T-cells are kept in a cell culture media at 37° C., 5% $CO_2$.

Preferably the time for contacting the T-cells with the peptide is in the range of from 6 hours to 6 days when the change of expression of a marker is studied. A suitable time is 5 days. When only binding of the peptide or peptide-MHC to T-cells is studied a shorter time for contacting can be used as known to a person skilled in the art.

The method of diagnosis quantifies the amount of T-cells that react with and become activated by the peptide thus immunologically "see" the peptide. The T-cells thus identified can be further characterized as regulatory or stimulating T-cells, or characterized in other ways, by using various markers.

Suitably the HLA genotype of the patient is determined as a first step, before reactivity of T-cells with peptides is determined. This may narrow down the number of peptides to be tested, as MHC with a certain genotype only bind to—and confer reactivity to—a certain set of peptides as described herein. The nature of the various HLA genotypes is known to a person skilled in the art.

Genotyping can be carried out for example by using PCR, sequencing of genomic DNA, southern blot, northern blot, or other methods known to a person in the art. For example, genotyping can be carried out as described in Olerup O, Zetterquist H. HLA-DR typing by PCR amplification with sequence-specific primers (PCR-SSP) in 2 hours: an alternative to serological DR typing in clinical practice including donor-recipient matching in cadaveric transplantation. Tissue Antigens 1992; 39:225-35.

Diagnosis can be carried out in vitro, that is, using T-cells isolated from the patient. The T-cells can be isolated from blood. In particular, a sample of PBMC (Peripheral Blood Mononuclear Cells) from a patient can be used. Thus the diagnosis can be carried out by contacting a sample of PBMCs with the peptide. PBMCs purified from about 10 ml of peripheral blood from the patient are sufficient to carry out the analysis. PBMC can be purified by methods known in the art, for example gradient centrifugation. In particular gradient centrifugation using Ficoll® can be used. Preferably the method removes plasma, polynuclear cells, and non-nucleated, cells such as red blood cells.

Conveniently, T-cells are characterized with the aid of markers. CD3 can be used as a general marker for all T-cells. CD4 can be used as a marker for T-helper cells (that is both effector T-cells and regulatory T-cells).

Activated effector T-cells can be identified by surface expression of for example CD 154 or CD69, or surface expression of MHC class II, proliferation and Ki67 staining. Suitable cytokines for detection of activation of T-effector cells is secretion of TNF alpha, interferon gamma, IL-17A, IL-17F, IL-2, IL-13 or IL-10.

Regulatory T-cells can be identified by the co-expression of CD4, CD25 and Foxp3. Activated regulatory T-cells can be identified by the up regulation of these markers.

Markers can conveniently be identified with the use of methods that are well known to a person skilled in the art. A suitable way to detect markers is using commercially available antibodies that are specific for those markers and which are labeled. There are many kinds of suitable labels, for example fluorescent labels or and enzymes, such as for example horse radish peroxidase.

Suitable methods for detecting markers include cytometry, luminex, elispot, ELISA or western blot. mRNA-based methods such as, for example, RT-PCR or northern blot can also be used for detecting markers.

When a naked peptide (that is, a peptide not bound to a MHC protein) is used for diagnosis, they can be added to cell cultures with PBMCs at a concentration of 2-100 ug/ml even more preferably 5-50 ug/ml. The PBMCs are then incubated with the peptides for a time period in the range of from 6 hours to 6 days, even more preferably 3-6 days and most preferably 5 days. The cells and/or cell culture media is subsequently analyzed for the markers as described above.

When peptide-MHC complexes are used for diagnosis, diagnosis can be carried out by using cell culture vessels, such as cell culture plates. For example, wells in a 96-well cell culture plate can be used. The cell culture vessel can be such that it allows the culturing of from 500 000 to 2 million cells. When peptide-MHC complexes are used, the surface of the cell culture vessel can be coated with the peptide-MHC complexes. A suitable concentration for use in coating the cell culture vessel with peptide-MHC complex is approximately 1-10 μg/ml). Conveniently, a cell culture plate comprises wells with a set of peptide-MHC complexes that are of interest for a patient with a particular HLA genotype. PBMCs are added to the well such that the T-cells can bind to the peptide-MHC complexes and become activated. A suitable time for incubation is in the range of from 6 hours to 6 days. The cells and/or cell culture media is subsequently analyzed for the markers as described above.

Suitably, diagnosis can be performed by using tetramers comprising the inventive peptides. A tetramer is a complex comprising a) one avidin or steptavidin molecule bound to b) four MHC molecules each carrying one peptide in the peptide binding cleft. The tetramer can be obtained by biotinlyation of the MHC protein and subsequently allowing the biotinlylated MHC protein to bind to straptavidin. Because streptavidin has four binding sites for biotin, a complex comprising one streptavidin molecule bound to four peptide-MHC complexes is formed, hence the name "tetramer". Snir et al, Arthritis & Rheumatism, Vol 63, NO 10 pp 2873-2883 and Novak et al, J Clin Invest 1999; 104: R63-7 provides details on production and use of tetramers. The tetramer can be conjugated to a label, such as a fluorescent label. The peptide-MHC complex will bind to T-cells that are involved in the regulation of rheumatoid arthritis because they express a T-cell receptor specific for the peptide. The T-cells can be detected by the label of the tetramer. One advantage with using tetramers is that that the signal is amplified because the tetramers bind stronger to the T-cells.

The fluorescent marker can be detected for example in a cytometric procedure such as FACS. Thus, the amount of T-cells that react with the peptide-MHC complex can be detected in a blood sample from a patient.

Thus, in yet another aspect of the invention it is provided a complex comprising a avidin or streptavidin molecule and a biotinylated peptide-MHC complex.

Alternatively, the method of diagnosis can comprise any one of the following steps: a) obtaining a sample of T-cells from an individual b) contacting the sample with a peptide or a peptide-MHC complex according to the invention, c) determining the binding of the peptide or the peptide-MHC complex to a population of T-cells in the sample. The method for diagnosis can also comprise a step of determining HLA genotype of the individual. The method for diagnosis is carried out in vitro, that is, it is not invasive.

In another embodiment the peptides can also be used to detect the presence or amount of antibodies against the epitopes present in the peptides. The presence of antibodies to a certain epitope is another means to qualify the nature of the autoimmunity of the patient. Thus, the method of diagnosis can comprise the steps of obtain a sample from the patient 2), contacting the sample with a peptide or peptide-MHC complex and 3) determining binding of antibodies in the sample to the peptide. The sample can be a sample of blood, serum, plasma, saliva or synovial fluid containing antibodies. There are various immunoassays that can be used for detecting binding of antibodies, examples of which are ELISA, western blot and radioimmunoassay but other methods can also be used.

In addition, the peptides and peptide-MHC complexes can be used as a research tool as described herein. For example, the peptides and peptide-MHC complexes can be used for monitoring the progression of rheumatoid arthritis, for grouping rheumatoid arthritis patients into subtypes and for correlating the clinical outcome to autoimmunity.

There is also provided a kit of parts comprising a peptide or a peptide-MHC complex according to the invention intended for use in diagnosis. Suitably, the kit also comprises other components, such as binding buffers, suitable for inclusion in a diagnostic kit. The kit may include one or more of the tetramer complexes described above. Conveniently, a group of peptides is provided in a kit for diagnostic testing, the kit comprising peptides or peptide-MHC-complexes of particular interest for a patient with a particular genotype as described above. By using such a kit, reactivity for a number of relevant peptides can be tested simultaneously. Optionally, the kit can comprise components for establishing the HLA genotype of the patient.

In one embodiment the kit comprises at least one cell-culture vessel that contain at least one peptide or peptide-MHC complex according to the invention. The kit can comprise several combined cell culture vessels such as the wells in a cell culture plate, where each well of the cell culture plate contains one type of peptide or peptide-MHC complex. Suitably each well of the cell culture plate is coated with peptide or peptide-MHC complex. When a naked peptide is used the peptide can be provided in lyophilized form in the cell culture vessel. The cell culture vessel is intended for the culture of cells, such that cells can survive for several days when kept in the vessel under appropriate conditions.

In another aspect of the invention there is provided a method for treatment of an autoimmune disease, in particular rheumatoid arthritis, comprising administering a peptide or a peptide-MHC complex according to the invention to a patient. The method of treatment can comprise the steps of 1) determining the HLA genotype of the patient as described herein and 2) determining the nature of the autoimmunity using the diagnostic method described herein 3) selecting the appropriate peptide (s) or peptide-MHC complex(s) for the patient, 4) administering the peptide or peptide-MHC complex to the patient, and optionally 5) monitoring the disease of the patient, preferably by using the diagnostic method provided herein. Such monitoring can include the ratio of regulatory T-cells to activating effector T-cells and changes is such ratio. Preferably a peptide that reacts with the T-cells is selected for treatment of the patient as such peptide will activate the regulatory T-cells. When a peptide-MHC complex is use the HLA genotype of the MHC protein is selected according to the genotype of the patient, as described herein.

The method of treatment can also comprise the step of determining which of the inventive peptide antigens and/or peptide-MHC complexes which are suitable for administration to the patient. Thus, the method can comprise the step of determining the nature of the autoimmune reactivity that is at least partly responsible for the disease. This step can be carried out by measuring T-cell activation as described herein or measuring the presence in the patient of antibodies that react with a certain peptide as described herein.

Suitably the patient is screened for autoimmunity by testing for autoimmunity against several different peptides. The method of treatment can comprise the step of determining which peptide and/or MHC protein-peptide complexes the autoantibody or autoantibodies that cause the disease is directed against.

FIGURES

FIG. 1. (A) CD4+ T cell responses to alpha-enolase (ENO) peptides in a HLA-DR*0401-positive patient. (B) CD4+ T cell responses to collagen-II (CII) peptides in a HLA-DR*1001-positive patient. PBMC from patients were cultured during 5 days with medium (white bar) or with two peptides (grey bars) or two corresponding citrullinated (CIT) variants (black bars). FACS analysis of co-expression of CD154 together with IFN-gamma and IL-17 on CD4+ T cells was carried out after in vitro stimulation of PBMCs with the indicated peptides (peptide reference numbers are shown). Further details are provided in Examples 13 and 15.

FIG. 2. PBMCs from a HLA-DRB1*0401-positive rheumatoid arthritis patient was stimulated with different enolase peptides for 5 days. Intracellular staining for cytokines was performed 6 hrs after restimulation and addition of Brefeldin A. The positive control (HA) primarily generate an IFNgamma response. The arginine versions of the a-enolase peptides does yield a response in this patient, while the citrullinated a-enolase peptides results in secretion of IL17A (all three peptides) and IFN gamma (one peptide). Further details are proved in Examples 4, 6 and 11.

FIG. 3. An HLA-DRB1*0401 tetramer loaded with the citrinullated enolase peptide 313 (SEQ ID NO 23) and labeled with the fluorochrome PE is used to stain PBMC from an *0401-positive rheumatoid arthritis patient. The cells in the upper right quadrant are T-cells with a T-cell receptor recognizing this particular peptide-MHC complex. Further details are proved in Examples 16 and 17.

EXAMPLES

Example 1

The inventors have identified peptides from human collagen type II, alpha-enolase and vimentin that specifically bind to the variants of MHC that are associated with a risk for developing rheumatoid arthritis and with a presence of antibodies to specific citrullinated proteins. These peptides bind to MHC with genotypes HLA DRB1 0101, 0401, 0404, 0405, 0408 and 1001 as indicated in tables 1, 2 and 3. Interestingly, none of the peptides bind to MHC with genotypes HLA-DR 03 and 0402, genotypes that are not associated with developing rheumatoid arthritis.

Binding of the peptides to recombinant MHC class II protein of various alleles has been confirmed in an in vitro binding assay and the results are shown in Tables 1, 2 and 3. In table 1, 2 and 3, the listing of the allele in the column for the allele indicates binding. Thus "0401" in the "Binds to 0401" column indicates binding of the peptide to MHC class II of the HLA DRB1 0401 genotype. "no" or no data indicates no binding to a protein of that genotype. Empty boxes indicate no binding or that binding has not been determined. In the tables it is also indicated if the peptide has a citrulline residue, where "yes" indicates the presence of a citrulline residue and "no" indicates the absence of a citrulline residue.

In addition, the inventors have identified previously unknown peptides from alpha-enolase (SEQ ID NO 15 to 22 and 24), and one citrullinated peptide from collagen type II (SEQ ID NO 30) that bind specifically HLA-DRB1 0401, were the non-citrullinated peptide did not bind. Thus for these peptides no binding to HLA-DR0401 was observed when citrulline was exchanged with the original amino acid arginine (Table 4). No binding of the citrullinated peptides was seen to HLA-DR 03 or 02 variants.

Thus peptides identified and presented in Table 4 bind to those variants of HLA-DR that associate with rheumatoid arthritis and anti-alpha-enolase and anti-collagen type II antibody responses (HLA-DRB1 0401 and/or 0404).

TABLE 1

| Protein | Peptide ref no | Binds to 0101 | Binds to 0401 | Binds to 0404 | Binds to 0405 | Binds to 0408 | Binds to 1001 | Citrinullation | SEQ ID NO |
|---|---|---|---|---|---|---|---|---|---|
| a-enolase | 1 | *0101 | no | *0404 | *0405 | no | *1001 | no | 1 |
| a-enolase | 6 | *0101 | no | *0404 | *0405 | no | no | no | 2 |
| a-enolase | 12 | *0101 | no | no | *0405 | *0408 | *1001 | no | 3 |
| a-enolase | 13 | *0101 | no | *0404 | no | no | no | no | 4 |
| a-enolase | 14 | *0101 | no | *0404 | no | *0408 | no | no | 5 |
| a-enolase | 15 | *0101 | no | *0404 | no | *0408 | no | no | 6 |
| a-enolase | 26 | *0101 | *0401 | *0404 | *0405 | *0408 | no | no | 7 |
| a-enolase | 34 | *0101 | *0401 | *0404 | *0405 | no | no | no | 8 |
| a-enolase | 38 | *0101 | *0401 | no | *0405 | *0408 | no | no | 9 |
| a-enolase | 57 | *0101 | *0401 | *0404 | *0405 | *0408 | *1001 | no | 10 |
| a-enolase | 66 | *0101 | *0401 | *0404 | *0405 | *0408 | no | no | 11 |
| a-enolase | 80 | *0101 | no | no | *0405 | *0408 | no | no | 12 |
| a-enolase | 81 | *0101 | no | *0404 | no | no | no | no | 13 |
| a-enolase | 287 | *0101 | *0401 | *0404 | *0405 | no | *1001 | yes | 14 |
| a-enolase | 289 | no | *0401 | no | *0405 | no | no | yes | 15 |
| a-enolase | 291 | *0101 | *0401 | *0404 | *0405 | no | *1001 | yes | 16 |
| a-enolase | 292 | *0101 | *0401 | *0404 | *0405 | no | no | yes | 17 |
| a-enolase | 297 | no | *0401 | no | *0405 | no | no | yes | 18 |
| a-enolase | 300 | no | *0401 | no | *0405 | no | no | yes | 19 |
| a-enolase | 301 | no | *0401 | *0404 | *0405 | no | no | yes | 20 |
| a-enolase | 302 | no | *0401 | *0404 | *0405 | no | no | yes | 21 |
| a-enolase | 305 | no | *0401 | no | *0405 | no | no | yes | 22 |
| a-enolase | 313 | *0101 | *0401 | *0404 | *0405 | no | no | yes | 23 |
| a-enolase | 324 | no | *0401 | *0404 | *0405 | no | no | yes | 24 |
| a-enolase | 36 | *0101 | no | no | *0405 | no | no | no | 32 |
| a-enolase | 45 | *0101 | *0401 | *0404 | *0405 | *0408 | no | no | 33 |
| a-enolase | 49 | no | *0401 | *0404 | *0405 | *0408 | no | no | 34 |
| a-enolase | 69 | no | no | no | *0405 | no | no | no | 35 |
| a-enolase | 299 | no | *0401 | no | *0405 | *0408 | no | yes | 36 |

TABLE 2

| Protein | Peptide ref no | Binds to 0101 | Binds to 0401 | Binds to 0404 | Binds to 0405 | Binds to 0408 | Binds to 1001 | Citrinullation | SEQ ID NO |
|---|---|---|---|---|---|---|---|---|---|
| type II collagen | 195 | | *0401 | *0404 | | | | no | 25 |
| type II collagen | 242 | *0101 | *0401 | *0404 | *0405 | | | no | 26 |
| type II collagen | 257 | | | *0404 | | | | no | 27 |
| type II collagen | 137 | *0101 | *0401 | *0404 | | | | no | 28 |
| type II collagen | 138 | *0101 | *0401 | | | | | no | 29 |
| type II collagen | 386 | | *0401 | *0404 | | | | yes | 30 |
| type II collagen | 411 | | *0401 | *0404 | *0405 | | | yes | 31 |
| type II collagen | 100 | | | *0404 | | | | no | 37 |
| type II collagen | 166 | | | *0404 | | | | no | 38 |
| type II collagen | 178 | | | | *0405 | | | no | 39 |
| type II collagen | 224 | | | *0404 | | | | no | 40 |
| type II collagen | 241 | | no | *0404 | *0405 | | | no | 41 |
| type II collagen | 263 | | | | | | *1001 | no | 42 |
| type II collagen | 268 | | | | | | *1001 | no | 43 |
| type II collagen | 272 | | | | *0405 | | | no | 44 |
| type II collagen | 332 | | *0401 | *0404 | *0405 | | | yes | 45 |
| type II collagen | 357 | | | | | | *1001 | yes | 46 |
| type II collagen | 362 | | | | | | *1001 | yes | 47 |
| type II collagen | 384 | | | | | *0408 | *1001 | yes | 48 |

TABLE 3

| Protein | Peptide ref no | Binds to 0101 | Binds to 0401 | Binds to 0404 | Binds to 0405 | Binds to 0408 | Binds to 1001 | Citrinullation | SEQ ID NO |
|---|---|---|---|---|---|---|---|---|---|
| vimentin | 1 | *0101 | *0401 | *0404 | no | | | no | 49 |
| vimentin | 3 | *0101 | *0401 | *0404 | *0405 | | | no | 50 |
| vimentin | 6 | | | | | | | no | 51 |
| vimentin | 13 | *0101 | no | | | | | no | 52 |
| vimentin | 14 | | | *0404 | | | | no | 53 |
| vimentin | 16 | no | *0401 | | | | | no | 54 |
| vimentin | 20 | | *0401 | | | | | no | 55 |
| vimentin | 27 | *0101 | | no | | | | no | 56 |
| vimentin | 32 | *0101 | | *0404 | | | | no | 57 |
| vimentin | 33 | no | *0401 | *0404 | no | | | no | 58 |
| vimentin | 34 | no | *0401 | | no | | | no | 59 |
| vimentin | 41 | | *0401 | *0404 | *0405 | | | no | 60 |
| vimentin | 42 | *0101 | *0401 | no | | | | no | 61 |
| vimentin | 44 | | | *0404 | | | | no | 62 |
| vimentin | 55 | *0101 | *0401 | | | | | no | 63 |
| vimentin | 59 | | *0401 | | | | | no | 64 |
| vimentin | 64 | *0101 | *0401 | | *0405 | | | no | 65 |
| vimentin | 71 | | *0401 | | | | | no | 66 |
| vimentin | 77 | *0101 | | | *0405 | | | no | 67 |
| vimentin | 79 | *0101 | no | *0404 | | | | no | 68 |
| vimentin | 81 | no | *0401 | no | no | | | no | 69 |
| vimentin | 92 | | | *0404 | | | | no | 70 |
| vimentin | 93 | no | *0401 | *0404 | | | | yes | 71 |
| vimentin | 95 | *0101 | *0401 | | | | | yes | 72 |
| vimentin | 98 | | *0401 | | *0405 | | | yes | 73 |
| vimentin | 99 | *0101 | *0401 | | | | | yes | 74 |
| vimentin | 104 | *0101 | *0401 | *0404 | no | | | yes | 75 |
| vimentin | 105 | *0101 | *0401 | no | no | | | yes | 76 |
| vimentin | 106 | *0101 | *0401 | *0404 | *0405 | | | yes | 77 |
| vimentin | 108 | no | *0401 | no | no | | | yes | 78 |
| vimentin | 111 | *0101 | *0401 | No | no | | | yes | 79 |
| vimentin | 117 | *0101 | | No | no | | | yes | 80 |
| vimentin | 132 | *0101 | | | | | | yes | 81 |
| vimentin | 133 | no | *0401 | No | no | | | yes | 82 |
| vimentin | 145 | | *0401 | | | | | yes | 83 |
| vimentin | 150 | | *0401 | | | | | yes | 84 |
| vimentin | 156 | *0101 | | | | | | yes | 85 |
| vimentin | 159 | | *0401 | No | | | | yes | 86 |
| vimentin | 166 | no | no | *0404 | no | | | yes | 87 |

TABLE 4

| Protein | Peptide no. | Binds to HLA subtype | Citrullination | Corresponding non-citrullinated peptide binds to HLA subtype: | Citrullination necessary for binding to these HLA genotypes: | SEQ ID NO |
|---|---|---|---|---|---|---|
| α-enolase | 287 | *0401 | yes | 0101, 0404 | 0401 | 14 |
| α-enolase | 289 | *0401 | yes | — | 0401 | 15 |
| α-enolase | 291 | *0401, *0404 | yes | 0404 | 0401 | 16 |
| α-enolase | 292 | *0401 | yes | — | 0401 | 17 |
| α-enolase | 297 | *0401 | yes | 0101 | 0401 | 18 |
| α-enolase | 300 | *0401 | yes | — | 0401 | 19 |
| α-enolase | 301 | *0401 | yes | 0404 | 0401 | 20 |
| α-enolase | 302 | *0401 | yes | — | 0401 | 21 |
| α-enolase | 305 | *0401 | yes | — | 0401 | 22 |
| α-enolase | 313 | *0401 | yes | 0101, 0401 | — | 23 |
| α-enolase | 324 | *0401 | yes | — | 0401 | 24 |
| type II collagen | 195 | *0404 | no | na | — | 25 |
| type II collagen | 242 | *0401, *0404 | no | na | — | 26 |
| type II collagen | 257 | *0404 | no | na | — | 27 |
| type II collagen | 137 | *0401 | no | na | — | 28 |
| type II collagen | 138 | *0401 | no | na | — | 29 |
| type II collagen | 386 | *0401 | yes | 0404 | 0401 | 30 |
| type II collagen | 411 | *0401, *0404 | yes | 0401, 0404 | — | 31 |

Example 2

PBMCs were isolated from several rheumatoid arthritis patients with HLA genotype HLA DRB1-0401. The citrinullated enolase peptide with SEQ ID NO 14 (peptide reference number 287) was added to the cells. As a negative control, cells were incubated without peptide. An influenza peptide was used as a positive control. The peptides were added at concentrations ranging from 5 to 50 ug/ml and after a 5-day incubation in a $CO_2$ incubator, cells were fixed, permeabilized and intracellular cytokine staining were performed. Antibodies for CD3, CD4, viable cells, CD154 (an activation marker) and cytokines IFNgamma, IL-17A and TNF alpha were used for analysis in a multiparameter flow cytometry panel. Cells from all patients exposed to the peptide double stained positive for both CD154 and at least one cytokine, which indicates that activation of T-cells has taken place.

Example 3

PBMCs were isolated from rheumatoid arthritis patients with HLA genotype HLA DRB1-0401. The citrinullated enolase peptide with SEQ ID NO 15 (peptide reference number 289) was added to the cells. As a negative control, cells were incubated without peptide. An influenza peptide was used as a positive control. In addition, the non-citrinullated version of the peptide was used as a negative control. The peptides were added at concentrations ranging from 5 to 50 ug/ml and after a 5-day incubation in a $CO_2$ incubator, cells were fixed, permeabilized and intracellular cytokine staining were performed. Antibodies for CD3, CD4, viable cells, CD154 (an activation marker) and cytokines IFNgamma, IL-17A and TNF alpha were used for analysis in a multiparameter flow cytometry panel. Cells from all patients exposed to the citrinullated peptide double stained positive for both CD154 and at least one cytokine, which indicates that activation of T-cells has taken place. The non-citrinullated peptide did not result in activation.

Example 4

PBMCs were isolated from rheumatoid arthritis patients with HLA genotype HLA DRB1-0401. The citrinullated enolase peptide with SEQ ID NO 16 (peptide reference number 291) was added to the cells. As a negative control, cells were incubated without peptide. An influenza peptide was used as a positive control. The peptides were added at concentrations ranging from 5 to 50 ug/ml and after a 5-day incubation in a $CO_2$ incubator, cells were fixed, permeabilized and intracellular cytokine staining were performed. Antibodies for CD3, CD4, viable cells, CD154 (an activation marker) and cytokines IFNgamma, IL-17A and TNF alpha were used for analysis in a multiparameter flow cytometry panel. Cells from all patients exposed to the citrinullated peptide double stained positive for both CD154 and at least one cytokine, which indicates that activation of T-cells has taken place. Data from one patient is shown in FIG. 2, which shows a strong increase in IL-17 compared to the controls. Data from one patient is shown in FIG. 2. The corresponding non-citrinullated peptide (peptide reference number 6, SEQ ID NO 2) did not result in a response, which could be expected because SEQ ID NO 2 does not bind MHC with genotype 0401 (Table 1).

Example 5

PBMCs were isolated from rheumatoid arthritis patients with HLA genotype HLA DRB1-0401. The citrinullated enolase peptide with SEQ ID NO 17 (peptide reference number 292) was added to the cells. As a negative control, cells were incubated without peptide. An influenza peptide was used as a positive control. In addition, the non-citrinullated version of the peptide was used as a negative control. The peptides were added at concentrations ranging from 5 to 50 ug/ml and after a 5-day incubation in a $CO_2$ incubator, cells were fixed, permeabilized and intracellular cytokine staining were performed. Antibodies for CD3, CD4, viable cells, CD154 (an activation marker) and cytokines IFNgamma, IL-17A and TNF alpha were used for analysis in a multiparameter flow cytometry panel. Cells from all patients exposed to the citrinullated peptide double stained positive for both CD154 and at least one cytokine, which indicates that activation of T-cells has taken place. The non-citrinullated peptide did not result in activation.

Example 6

PBMCs were isolated from rheumatoid arthritis patients with HLA genotype HLA DRB1-0401. The citrinullated enolase peptide with SEQ ID NO 18 (peptide reference number 297) was added to the cells. As a negative control, cells were incubated without peptide. An influenza peptide was used as a positive control. The peptides were added at concentrations ranging from 5 to 50 ug/ml and after a 5-day incubation in a $CO_2$ incubator, cells were fixed, permeabilized and intracellular cytokine staining were performed. Antibodies for CD3, CD4, viable cells, CD154 (an activation marker) and cytokines IFNgamma, IL-17A and TNF alpha were used for analysis in a multiparameter flow cytometry panel. Cells from all patients exposed to the citrinullated peptide double stained positive for both CD154 and at least one cytokine, which indicates that activation of T-cells has taken place. Data from one patient is shown in FIG. 2 which shows a strong increase in IFN gamma and IL-17 compared to the controls. Data from one patient is shown in FIG. 2.

Example 7

PBMCs were isolated from rheumatoid arthritis patients with HLA genotype HLA DRB1-0401. The citrinullated enolase peptide with SEQ ID NO 19 (peptide reference number 300) was added to the cells. As a negative control, cells were incubated without peptide. An influenza peptide was used as a positive control. In addition, the non-citrinullated version of the peptide was used as a negative control. The peptides were added at concentrations ranging from 5 to 50 ug/ml and after a 5-day incubation in a $CO_2$ incubator, cells were fixed, permeabilized and intracellular cytokine staining were performed. Antibodies for CD3, CD4, viable cells, CD154 (an activation marker) and cytokines IFNgamma, IL-17A and TNF alpha were used for analysis in a multiparameter flow cytometry panel. Cells from all patients exposed to the citrinullated peptide double stained positive for both CD154 and at least one cytokine, which indicates that activation of T-cells has taken place. The non-citrinullated peptide did not result in activation.

Example 8

PBMCs were isolated from rheumatoid arthritis patients with HLA genotype HLA DRB1-0401. The citrinullated enolase peptide with SEQ ID NO 20 (peptide reference number 301) was added to the cells. As a negative control, cells were incubated without peptide. An influenza peptide was used as a positive control. The peptides were added at concentrations ranging from 5 to 50 ug/ml and after a 5-day incubation in a $CO_2$ incubator, cells were fixed, permeabilized and intracellular cytokine staining were performed. Antibodies for CD3, CD4, viable cells, CD154 (an activation marker) and cytokines IFNgamma, IL-17A and TNF alpha were used for analysis in a multiparameter flow cytometry panel. Cells from all patients exposed to the citrinullated peptide double stained positive for both CD154 and at least one cytokine, which indicates that activation of T-cells has taken place.

Example 9

PBMCs were isolated from rheumatoid arthritis patients with HLA genotype HLA DRB1-0401. The citrinullated enolase peptide with SEQ ID NO 21 (peptide reference number 302) was added to the cells. As a negative control, cells were incubated without peptide. An influenza peptide was used as a positive control. In addition, the non-citrinulated version of the peptide was used as a negative control. The peptides were added at concentrations ranging from 5 to 50 ug/ml and after a 5-day incubation in a $CO_2$ incubator, cells were fixed, permeabilized and intracellular cytokine staining were performed. Antibodies for CD3, CD4, viable cells, CD154 (an activation marker) and cytokines IFNgamma, IL-17A and TNF alpha were used for analysis in a multiparameter flow cytometry panel. Cells from all patients exposed to the citrinullated peptide double stained positive for both CD154 and at least one cytokine, which indicates that activation of T-cells has taken place. The non-citrinullated peptide did not result in activation.

Example 10

PBMCs were isolated from rheumatoid arthritis patients with HLA genotype HLA DRB1-0401. The non-citrinullated enolase peptide with SEQ ID NO 34 (peptide reference number 49) was added to the cells. As a negative control, cells were incubated without peptide. An influenza peptide was used as a positive control. The peptides were added at concentrations ranging from 5 to 50 ug/ml and after a 5-day incubation in a $CO_2$ incubator, cells were fixed, permeabilized and intracellular cytokine staining were performed. Antibodies for CD3, CD4, viable cells, CD154 (an activation marker) and cytokines IFNgamma, IL-17A and TNF alpha were used for analysis in a multiparameter flow cytometry panel. Cells from all patients exposed to the citrinullated peptide double stained positive for both CD154 and at least one cytokine, which indicates that activation of T-cells has taken place.

Example 11

PBMCs were isolated from rheumatoid arthritis patients with HLA genotype HLA DRB1-0401. The citrinullated enolase peptide with SEQ ID NO 22 (peptide reference number 305) was added to the cells. As a negative control, cells were incubated without peptide. An influenza peptide was used as a positive control. The peptides were added at concentrations ranging from 5 to 50 ug/ml and after a 5-day incubation in a $CO_2$ incubator, cells were fixed, permeabilized and intracellular cytokine staining were performed. Antibodies for CD3, CD4, viable cells, CD154 (an activation marker) and cytokines IFNgamma, IL-17A and TNF alpha were used for analysis in a multiparameter flow cytometry panel. Cells from all patients exposed to the citrinullated peptide double stained positive for both CD154 and at least one cytokine, which indicates that activation of T-cells has taken place. Data from one patient is shown in FIG. 2.

Example 12

PBMCs were isolated from rheumatoid arthritis patients with HLA genotype HLA DRB1-0401. The non-citrinullated enolase peptide with SEQ ID NO 11 (peptide reference number 66) was added to the cells. As a negative control, cells were incubated without peptide. An influenza peptide was used as a positive control. The peptides were added at concentrations ranging from 5 to 50 ug/ml and after a 5-day incubation in a $CO_2$ incubator, cells were fixed, permeabilized and intracellular cytokine staining were performed. Antibodies for CD3, CD4, viable cells, CD154 (an activation marker) and cytokines IFNgamma, IL-17A and TNF alpha were used for analysis in a multiparameter flow cytometry panel. Cells from all patients exposed to the citrinullated peptide double stained positive for both CD154 and at least one cytokine, which indicates that activation of T-cells has taken place.

Example 13

PBMCs were isolated from rheumatoid arthritis patients with HLA genotype HLA DRB1-0401. The citrinullated enolase peptide with SEQ ID NO 23 (peptide reference number 313) was added to the cells. As a negative control, cells were incubated without peptide. An influenza peptide was used as a positive control. The peptides were added at concentrations ranging from 5 to 50 ug/ml and after a 5-day incubation in a $CO_2$ incubator, cells were fixed, permeabilized and intracellular cytokine staining were performed. Antibodies for CD3, CD4, viable cells, CD154 (an activation marker) and cytokines IFNgamma, IL-17A and TNF alpha were used for analysis in a multiparameter flow cytometry panel. Cells from all patients exposed to the citrinullated peptide double stained positive for both CD154 and at least one cytokine, which indicates that activation of T-cells has taken place. Data from one patient is shown in FIG. 1A.

Example 14

PBMCs were isolated from rheumatoid arthritis patients with HLA genotype HLA DRB1-0401. The citrinullated enolase peptide with SEQ ID NO 24 (peptide reference number 324) was added to the cells. As a negative control, cells were incubated without peptide. An influenza peptide was used as a positive control. In addition, the non-citrinulated version of the peptide was used as a negative control. The peptides were added at concentrations ranging from 5 to 50 ug/ml and after a 5-day incubation in a $CO_2$ incubator, cells were fixed, permeabilized and intracellular cytokine staining were performed. Antibodies for CD3, CD4, viable cells, CD154 (an activation marker) and cytokines IFNgamma, IL-17A and TNF alpha were used for analysis in a multiparameter flow cytometry panel. Cells from all patients exposed to the citrinullated peptide double stained positive for both CD154 and at least one cytokine, which indicates that activation of T-cells has taken place. The non-citrinullated peptide did not result in activation.

Example 15

PBMCs were isolated from rheumatoid arthritis patients with HLA genotype HLA DRB1-1001. The citrinullated collagen type II-peptide with SEQ ID NO 46 (peptide reference number 357) was added to the cells. As a negative control, cells were incubated without peptide. An influenza peptide was used as a positive control. In addition, the non-citrinullated version of the peptide was used as a negative control (peptide reference number 148). The peptides were added at concentrations ranging from 5 to 50 ug/ml and after a 5-day incubation in a $CO_2$ incubator, cells were fixed, permeabilized and intracellular cytokine staining were performed. Antibodies for CD3, CD4, viable cells, CD154 (an activation marker) and cytokines IFNgamma, IL-17A and TNF alpha were used for analysis in a multi-parameter flow cytometry panel. Cells from all patients exposed to the citrinullated peptide double stained positive for both CD154 and at least one cytokine, which indicates that activation of T-cells has taken place. The non-citrinullated peptide did not result in activation. Data from one patient is shown in FIG. 1 B.

Examples 2-15

Data is from examples 2-15 are summarized in table 5. Activation of T-cells means that all patients are positive for at least one cytokine. This is not necessarily indicated in FIGS. 1A and B, which show selected data from individual patients for selected cytokines.

TABLE 5

| Protein | Peptide ref no | HLA tested | Citrinullation | Binds MHC in vitro | Activation of T-cells | SEQ ID NO |
|---|---|---|---|---|---|---|
| a-enolase | 66 | *0401 | no | yes | yes | 11 |
| a-enolase | 287 | *0401 | yes | yes | yes | 14 |
| a-enolase | 289 | *0401 | yes | yes | yes | 15 |
| a-enolase | 291 | *0401 | yes | yes | yes | 16 |
| a-enolase | 292 | *0401 | yes | yes | yes | 17 |
| a-enolase | 297 | *0401 | yes | yes | yes | 18 |
| a-enolase | 300 | *0401 | yes | yes | yes | 19 |

TABLE 5-continued

| Protein | Peptide ref no | HLA tested | Citrinullation | Binds MHC in vitro | Activation of T-cells | SEQ ID NO |
|---|---|---|---|---|---|---|
| a-enolase | 301 | *0401 | yes | yes | yes | 20 |
| a-enolase | 302 | *0401 | yes | yes | yes | 21 |
| a-enolase | 305 | *0401 | yes | yes | yes | 22 |
| a-enolase | 313 | *0401 | yes | yes | yes | 23 |
| a-enolase | 324 | *0401 | yes | yes | yes | 24 |
| a-enolase | 49 | *0401 | no | yes | yes | 34 |
| type II collagen | 357 | *1001 | yes | yes | yes | 46 |

Example 16

Production of peptide-MHC complex: Recombinant HLA-DRB1 *0401 was produced as described in Novak et al, J Clin Invest 1999; 104: R63-7. Briefly soluble DR0401 was purified from insect cell culture supernatants and biotinylated at a sequence specific site using biotin ligase (Avidity) prior to dialysis into phosphate storage buffer. The biotinylated monomer was loaded with 0.2 mg/ml of the peptide with SEQ ID NO 23 (peptide reference number 313) by incubation at 37° C. for 72 hours in the presence of 2.5 mg/ml n-octyl-beta-D-glucopyranoside and 1 mM Prefabloc SC (Sigma-Aldrich).

Example 17

Production and use of tetramers. The peptide-MHC complexes in Example 16 were conjugated to tetramers using R-phycoerythrin-streptavidin (Invitrogen) at a molar ratio of 8:1. PBMCs from one patient with rheumatoid arthritis, HLA type *0401, was stained using the tetramers and immediately analyzed by FACS. Several CD4 positive T-helper cells were identified. It could be estimated that about 1 out of 350 000 CD4 positive cells reacted with the peptide, which indicates as significant immune response. Data is presented in FIG. 3, where cells in the upper-right corner bind to the peptide-MHC complex.

I claim:

1. A complex of a human recombinant MHC class II protein fragment of HLA-DRB1 *1001 and the synthesized or recombinantly produced peptide consisting of SEQ ID NO 46, wherein said fragment of said human recombinant MEW class II protein excludes at least the transmembrane domains of said MEW class II protein and is stabilized by at least one of: retaining parts of the alpha 2 and beta 2 inner domains, introducing a leucine zipper structure to the inner domains, introducing cysteine residues that form disulfide bridges linking the alpha and the beta chains, and introducing a peptide in the peptide binding groove that is covalently linked to an elongation of the beta domain.

2. A kit of parts comprising the complex of claim 1.

3. The kit according to claim 2 additionally comprising at least one cell culture vessel.

4. The kit according to claim 2 comprising means for detecting the expression of at least one protein selected from the group consisting of CD3, CD4, Foxp3, CD25, TNF alpha, interferon gamma, interleukin-17A, interleukin-17F, CD154, CD69, Ki 67, interleukin-2, interleukin-13 and interleukin-10.

5. The kit according to claim 4 where the means for detection is an antibody against said protein.

6. The kit according to claim 4 where the means for detection is a set of primers for RT-PCR.

7. A composition comprising the complex of claim 1 and an additive or excipient.

8. The complex of claim 1, wherein said complex is stable in solution.

9. The complex of claim 8, wherein said human recombinant WIC class II protein fragment excluding said transmembrane domains is stabilized by retaining parts of the alpha 2 and beta 2 inner domains.

10. The complex of claim 8, wherein the inner domains of said human recombinant WIC class II protein fragment excluding said transmembrane domains are stabilized by the introduction of a leucine zipper structure.

11. The complex of claim 8, wherein said human recombinant WIC class II protein fragment excluding said transmembrane domains is stabilized by introducing cysteine residues that form disulfide bridges linking the alpha and the beta chains.

12. The complex of claim 8, wherein said human recombinant WIC class II protein fragment excluding said transmembrane domains is stabilized by introducing a peptide in the peptide binding groove that is covalently linked to an elongation of the beta domain.

* * * * *

UNITED STATES PATENT AND TRADEMARK OFFICE
CERTIFICATE OF CORRECTION

PATENT NO.          : 10,774,129 B2                         Page 1 of 1
APPLICATION NO.     : 14/953484
DATED               : September 15, 2020
INVENTOR(S)         : Rikard Holmdahl It is certified that error appears in the above-identified patent and that said Letters Patent is hereby corrected as shown below:

In the Claims

Column 55, Claim 1, Line 39:
Currently reads "MEW"
Where it should read --MHC--.

Column 55, Claim 1, Line 40:
Currently reads "MEW"
Where it should read --MHC--.

Column 56, Claim 9, Line 40:
Currently reads "WIC"
Where it should read --MHC--.

Column 56, Claim 10, Line 44:
Currently reads "WIC"
Where it should read --MHC--.

Column 56, Claim 11, Line 48:
Currently reads "WIC"
Where it should read --MHC--.

Column 56, Claim 12, Line 53:
Currently reads "WIC"
Where it should read --MHC--.

Signed and Sealed this
Tenth Day of November, 2020

Andrei Iancu
*Director of the United States Patent and Trademark Office*

SEQUENCE LISTING

<160> NUMBER OF SEQ ID NOS: 87

<210> SEQ ID NO 1
<211> LENGTH: 15
<212> TYPE: PRT
<213> ORGANISM: Homo sapiens

<400> SEQUENCE: 1

Met Ser Ile Leu Lys Ile His Ala Arg Glu Ile Phe Asp Ser Arg
1               5                   10                  15

<210> SEQ ID NO 2
<211> LENGTH: 15
<212> TYPE: PRT
<213> ORGANISM: Homo sapiens

<400> SEQUENCE: 2

Thr Ser Lys Gly Leu Phe Arg Ala Ala Val Pro Ser Gly Ala Ser
1               5                   10                  15

<210> SEQ ID NO 3
<211> LENGTH: 15
<212> TYPE: PRT
<213> ORGANISM: Homo sapiens

```
<400> SEQUENCE: 3

Arg Tyr Met Gly Lys Gly Val Ser Lys Ala Val Glu His Ile Asn
1               5                   10                  15

<210> SEQ ID NO 4
<211> LENGTH: 15
<212> TYPE: PRT
<213> ORGANISM: Homo sapiens

<400> SEQUENCE: 4

Gly Val Ser Lys Ala Val Glu His Ile Asn Lys Thr Ile Ala Pro
1               5                   10                  15

<210> SEQ ID NO 5
<211> LENGTH: 15
<212> TYPE: PRT
<213> ORGANISM: Homo sapiens

<400> SEQUENCE: 5

Val Glu His Ile Asn Lys Thr Ile Ala Pro Ala Leu Val Ser Lys
1               5                   10                  15

<210> SEQ ID NO 6
<211> LENGTH: 15
<212> TYPE: PRT
<213> ORGANISM: Homo sapiens

<400> SEQUENCE: 6

Lys Thr Ile Ala Pro Ala Leu Val Ser Lys Lys Leu Asn Val Thr
1               5                   10                  15

<210> SEQ ID NO 7
<211> LENGTH: 15
<212> TYPE: PRT
<213> ORGANISM: Homo sapiens

<400> SEQUENCE: 7

Lys Gly Val Pro Leu Tyr Arg His Ile Ala Asp Leu Ala Gly Asn
1               5                   10                  15

<210> SEQ ID NO 8
<211> LENGTH: 15
<212> TYPE: PRT
<213> ORGANISM: Homo sapiens

<400> SEQUENCE: 8

Gln Glu Phe Met Ile Leu Pro Val Gly Ala Ala Asn Phe Arg Glu
1               5                   10                  15

<210> SEQ ID NO 9
<211> LENGTH: 15
<212> TYPE: PRT
<213> ORGANISM: Homo sapiens

<400> SEQUENCE: 9

Ala Glu Val Tyr His Asn Leu Lys Asn Val Ile Lys Glu Lys Tyr
1               5                   10                  15

<210> SEQ ID NO 10
<211> LENGTH: 15
<212> TYPE: PRT
<213> ORGANISM: Homo sapiens

<400> SEQUENCE: 10
```

```
Lys Ser Phe Ile Lys Asp Tyr Pro Val Val Ser Ile Glu Asp Pro
1               5                   10                  15

<210> SEQ ID NO 11
<211> LENGTH: 15
<212> TYPE: PRT
<213> ORGANISM: Homo sapiens

<400> SEQUENCE: 11

Lys Arg Ile Ala Lys Ala Val Asn Glu Lys Ser Cys Asn Cys Leu
1               5                   10                  15

<210> SEQ ID NO 12
<211> LENGTH: 15
<212> TYPE: PRT
<213> ORGANISM: Homo sapiens

<400> SEQUENCE: 12

Gly Ala Pro Cys Arg Ser Glu Arg Leu Ala Lys Tyr Asn Gln Leu
1               5                   10                  15

<210> SEQ ID NO 13
<211> LENGTH: 15
<212> TYPE: PRT
<213> ORGANISM: Homo sapiens

<400> SEQUENCE: 13

Ser Glu Arg Leu Ala Lys Tyr Asn Gln Leu Leu Arg Ile Glu Glu
1               5                   10                  15

<210> SEQ ID NO 14
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (15)..(15)
<223> OTHER INFORMATION: Citrulline

<400> SEQUENCE: 14

Met Ser Ile Leu Lys Ile His Ala Xaa Glu Ile Phe Asp Ser Xaa
1               5                   10                  15

<210> SEQ ID NO 15
<211> LENGTH: 15
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Citrulline

<400> SEQUENCE: 15

Ile Phe Asp Ser Xaa Gly Asn Pro Thr Val Glu Val Asp Leu Phe
1               5                   10                  15

<210> SEQ ID NO 16
<211> LENGTH: 15
<212> TYPE: PRT
<213> ORGANISM: Homo sapiens
<220> FEATURE:
<221> NAME/KEY: MOD_RES
<222> LOCATION: (7)..(7)
```

```
<223> OTHER INFORMATION: Citrulline

<400> SEQUENCE: 16

Thr Ser Lys Gly Leu Phe Xaa Ala Ala Val Pro Ser Gly Ala Ser
1               5                   10                  15

<210> SEQ ID NO 17
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Citrulline

<400> SEQUENCE: 17

Phe Xaa Ala Ala Val Pro Ser Gly Ala Ser Thr Gly Ile Tyr Glu
1               5                   10                  15

<210> SEQ ID NO 18
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Citrulline

<400> SEQUENCE: 18

Xaa Tyr Met Gly Lys Gly Val Ser Lys Ala Val Glu His Ile Asn
1               5                   10                  15

<210> SEQ ID NO 19
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Citrulline

<400> SEQUENCE: 19

Tyr Xaa His Ile Ala Asp Leu Ala Gly Asn Ser Glu Val Ile Leu
1               5                   10                  15

<210> SEQ ID NO 20
<211> LENGTH: 15
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Citrulline

<400> SEQUENCE: 20

Gln Glu Phe Met Ile Leu Pro Val Gly Ala Ala Asn Phe Xaa Glu
1               5                   10                  15

<210> SEQ ID NO 21
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (13)..(13)
```

```
<223> OTHER INFORMATION: Citrulline

<400> SEQUENCE: 21

Leu Pro Val Gly Ala Ala Asn Phe Xaa Glu Ala Met Xaa Ile Gly
1               5                   10                  15

<210> SEQ ID NO 22
<211> LENGTH: 15
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Citrulline

<400> SEQUENCE: 22

Val Ile Gly Met Asp Val Ala Ala Ser Glu Phe Phe Xaa Ser Gly
1               5                   10                  15

<210> SEQ ID NO 23
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Citrulline

<400> SEQUENCE: 23

Lys Xaa Ile Ala Lys Ala Val Asn Glu Lys Ser Cys Asn Cys Leu
1               5                   10                  15

<210> SEQ ID NO 24
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Citrulline
<220> FEATURE:
<221> NAME/KEY: MOD_RES
<222> LOCATION: (10)..(10)
<223> OTHER INFORMATION: Citrulline

<400> SEQUENCE: 24

Lys Ala Lys Phe Ala Gly Xaa Asn Phe Xaa Asn Pro Leu Ala Lys
1               5                   10                  15

<210> SEQ ID NO 25
<211> LENGTH: 15
<212> TYPE: PRT
<213> ORGANISM: Homo sapiens

<400> SEQUENCE: 25

Pro Gly Leu Gln Gly Met Pro Gly Glu Arg Gly Ala Ala Gly Ile
1               5                   10                  15

<210> SEQ ID NO 26
<211> LENGTH: 15
<212> TYPE: PRT
<213> ORGANISM: Homo sapiens

<400> SEQUENCE: 26

Gly Ile Val Gly Leu Pro Gly Gln Arg Gly Glu Arg Gly Phe Pro
1               5                   10                  15
```

-continued

```
<210> SEQ ID NO 27
<211> LENGTH: 15
<212> TYPE: PRT
<213> ORGANISM: Homo sapiens

<400> SEQUENCE: 27

Gly Asp Arg Gly Glu Thr Gly Ala Val Gly Ala Pro Gly Ala Pro
1               5                   10                  15

<210> SEQ ID NO 28
<211> LENGTH: 15
<212> TYPE: PRT
<213> ORGANISM: Homo sapiens

<400> SEQUENCE: 28

Gly Glu Pro Gly Ile Ala Gly Phe Lys Gly Glu Gln Gly Pro Lys
1               5                   10                  15

<210> SEQ ID NO 29
<211> LENGTH: 15
<212> TYPE: PRT
<213> ORGANISM: Homo sapiens

<400> SEQUENCE: 29

Ala Gly Phe Lys Gly Glu Gln Gly Pro Lys Gly Glu Pro Gly Pro
1               5                   10                  15

<210> SEQ ID NO 30
<211> LENGTH: 15
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Citrulline

<400> SEQUENCE: 30

Pro Gly Leu Gln Gly Met Pro Gly Glu Xaa Gly Ala Ala Gly Ile
1               5                   10                  15

<210> SEQ ID NO 31
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (12)..(12)
<223> OTHER INFORMATION: Citrulline

<400> SEQUENCE: 31

Gly Ile Val Gly Leu Pro Gly Gln Xaa Gly Glu Xaa Gly Phe Pro
1               5                   10                  15

<210> SEQ ID NO 32
<211> LENGTH: 15
<212> TYPE: PRT
<213> ORGANISM: Homo sapiens

<400> SEQUENCE: 32

Ala Asn Phe Arg Glu Ala Met Arg Ile Gly Ala Glu Val Tyr His
1               5                   10                  15

<210> SEQ ID NO 33
```

-continued

```
<211> LENGTH: 15
<212> TYPE: PRT
<213> ORGANISM: Homo sapiens

<400> SEQUENCE: 33

Lys Glu Gly Leu Glu Leu Leu Lys Thr Ala Ile Gly Lys Ala Gly
1               5                   10                  15

<210> SEQ ID NO 34
<211> LENGTH: 15
<212> TYPE: PRT
<213> ORGANISM: Homo sapiens

<400> SEQUENCE: 34

Val Ile Gly Met Asp Val Ala Ala Ser Glu Phe Phe Arg Ser Gly
1               5                   10                  15

<210> SEQ ID NO 35
<211> LENGTH: 15
<212> TYPE: PRT
<213> ORGANISM: Homo sapiens

<400> SEQUENCE: 35

Leu Leu Lys Val Asn Gln Ile Gly Ser Val Thr Glu Ser Leu Gln
1               5                   10                  15

<210> SEQ ID NO 36
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Citrulline

<400> SEQUENCE: 36

Lys Gly Val Pro Leu Tyr Xaa His Ile Ala Asp Leu Ala Gly Asn
1               5                   10                  15

<210> SEQ ID NO 37
<211> LENGTH: 15
<212> TYPE: PRT
<213> ORGANISM: Homo sapiens

<400> SEQUENCE: 37

Pro Gln Gly Ala Arg Gly Phe Pro Gly Thr Pro Gly Leu Pro Gly
1               5                   10                  15

<210> SEQ ID NO 38
<211> LENGTH: 15
<212> TYPE: PRT
<213> ORGANISM: Homo sapiens

<400> SEQUENCE: 38

Val Met Gly Phe Pro Gly Pro Lys Gly Ala Asn Gly Glu Pro Gly
1               5                   10                  15

<210> SEQ ID NO 39
<211> LENGTH: 15
<212> TYPE: PRT
<213> ORGANISM: Homo sapiens

<400> SEQUENCE: 39

Pro Ser Gly Phe Gln Gly Leu Pro Gly Pro Pro Gly Pro Pro Gly
1               5                   10                  15
```

```
<210> SEQ ID NO 40
<211> LENGTH: 15
<212> TYPE: PRT
<213> ORGANISM: Homo sapiens

<400> SEQUENCE: 40

Gly Pro Pro Gly Ala Thr Gly Phe Pro Gly Ala Ala Gly Arg Val
1               5                   10                  15

<210> SEQ ID NO 41
<211> LENGTH: 15
<212> TYPE: PRT
<213> ORGANISM: Homo sapiens

<400> SEQUENCE: 41

Leu Ala Gly Gln Arg Gly Ile Val Gly Leu Pro Gly Gln Arg Gly
1               5                   10                  15

<210> SEQ ID NO 42
<211> LENGTH: 15
<212> TYPE: PRT
<213> ORGANISM: Homo sapiens

<400> SEQUENCE: 42

Gly Asp Arg Gly Glu Ala Gly Ala Gln Gly Pro Met Gly Pro Ser
1               5                   10                  15

<210> SEQ ID NO 43
<211> LENGTH: 15
<212> TYPE: PRT
<213> ORGANISM: Homo sapiens

<400> SEQUENCE: 43

Pro Gln Gly Pro Arg Gly Asp Lys Gly Glu Ala Gly Glu Pro Gly
1               5                   10                  15

<210> SEQ ID NO 44
<211> LENGTH: 15
<212> TYPE: PRT
<213> ORGANISM: Homo sapiens

<400> SEQUENCE: 44

Gly His Arg Gly Phe Thr Gly Leu Gln Gly Leu Pro Gly Pro Pro
1               5                   10                  15

<210> SEQ ID NO 45
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Citrulline
<220> FEATURE:
<221> NAME/KEY: MOD_RES
<222> LOCATION: (10)..(10)
<223> OTHER INFORMATION: Citrulline

<400> SEQUENCE: 45

Xaa Gly Pro Pro Gly Pro Gln Gly Ala Xaa Gly Phe Pro Gly Thr
1               5                   10                  15

<210> SEQ ID NO 46
<211> LENGTH: 15
<212> TYPE: PRT
<213> ORGANISM: Homo sapiens
```

```
<220> FEATURE:
<221> NAME/KEY: MOD_RES
<222> LOCATION: (5)..(5)
<223> OTHER INFORMATION: Citrulline

<400> SEQUENCE: 46

Ala Pro Gly Asn Xaa Gly Phe Pro Gly Gln Asp Gly Leu Ala Gly
1               5                   10                  15

<210> SEQ ID NO 47
<211> LENGTH: 15
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Citrulline

<400> SEQUENCE: 47

Pro Lys Gly Ala Asn Gly Asp Pro Gly Xaa Pro Gly Glu Pro Gly
1               5                   10                  15

<210> SEQ ID NO 48
<211> LENGTH: 15
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Citrulline

<400> SEQUENCE: 48

Gln Gly Pro Xaa Gly Leu Pro Gly Thr Pro Gly Thr Asp Gly Pro
1               5                   10                  15

<210> SEQ ID NO 49
<211> LENGTH: 15
<212> TYPE: PRT
<213> ORGANISM: Homo sapiens

<400> SEQUENCE: 49

Met Ser Thr Arg Ser Val Ser Ser Ser Ser Tyr Arg Arg Met Phe
1               5                   10                  15

<210> SEQ ID NO 50
<211> LENGTH: 15
<212> TYPE: PRT
<213> ORGANISM: Homo sapiens

<400> SEQUENCE: 50

Tyr Arg Arg Met Phe Gly Gly Pro Gly Thr Ala Ser Arg Pro Ser
1               5                   10                  15

<210> SEQ ID NO 51
<211> LENGTH: 15
<212> TYPE: PRT
<213> ORGANISM: Homo sapiens

<400> SEQUENCE: 51

Ser Ser Arg Ser Tyr Val Thr Thr Ser Thr Arg Thr Tyr Ser Leu
1               5                   10                  15

<210> SEQ ID NO 52
<211> LENGTH: 15
<212> TYPE: PRT
<213> ORGANISM: Homo sapiens
```

```
<400> SEQUENCE: 52

Tyr Ala Thr Arg Ser Ser Ala Val Arg Leu Arg Ser Ser Val Pro
1               5                   10                  15

<210> SEQ ID NO 53
<211> LENGTH: 15
<212> TYPE: PRT
<213> ORGANISM: Homo sapiens

<400> SEQUENCE: 53

Ser Ala Val Arg Leu Arg Ser Ser Val Pro Gly Val Arg Leu Leu
1               5                   10                  15

<210> SEQ ID NO 54
<211> LENGTH: 15
<212> TYPE: PRT
<213> ORGANISM: Homo sapiens

<400> SEQUENCE: 54

Gly Val Arg Leu Leu Gln Asp Ser Val Asp Phe Ser Leu Ala Asp
1               5                   10                  15

<210> SEQ ID NO 55
<211> LENGTH: 15
<212> TYPE: PRT
<213> ORGANISM: Homo sapiens

<400> SEQUENCE: 55

Phe Lys Asn Thr Arg Thr Asn Glu Lys Val Glu Leu Gln Glu Leu
1               5                   10                  15

<210> SEQ ID NO 56
<211> LENGTH: 15
<212> TYPE: PRT
<213> ORGANISM: Homo sapiens

<400> SEQUENCE: 56

Leu Leu Ala Glu Leu Glu Gln Leu Lys Gly Gln Gly Lys Ser Arg
1               5                   10                  15

<210> SEQ ID NO 57
<211> LENGTH: 15
<212> TYPE: PRT
<213> ORGANISM: Homo sapiens

<400> SEQUENCE: 57

Glu Leu Arg Arg Gln Val Asp Gln Leu Thr Asn Asp Lys Ala Arg
1               5                   10                  15

<210> SEQ ID NO 58
<211> LENGTH: 15
<212> TYPE: PRT
<213> ORGANISM: Homo sapiens

<400> SEQUENCE: 58

Val Asp Gln Leu Thr Asn Asp Lys Ala Arg Val Glu Val Glu Arg
1               5                   10                  15

<210> SEQ ID NO 59
<211> LENGTH: 15
<212> TYPE: PRT
<213> ORGANISM: Homo sapiens

<400> SEQUENCE: 59
```

Asn Asp Lys Ala Arg Val Glu Val Glu Arg Asp Asn Leu Ala Glu
1               5                   10                  15

<210> SEQ ID NO 60
<211> LENGTH: 15
<212> TYPE: PRT
<213> ORGANISM: Homo sapiens

<400> SEQUENCE: 60

Asn Thr Leu Gln Ser Phe Arg Gln Asp Val Asp Asn Ala Ser Leu
1               5                   10                  15

<210> SEQ ID NO 61
<211> LENGTH: 15
<212> TYPE: PRT
<213> ORGANISM: Homo sapiens

<400> SEQUENCE: 61

Phe Arg Gln Asp Val Asp Asn Ala Ser Leu Ala Arg Leu Asp Leu
1               5                   10                  15

<210> SEQ ID NO 62
<211> LENGTH: 15
<212> TYPE: PRT
<213> ORGANISM: Homo sapiens

<400> SEQUENCE: 62

Ala Arg Leu Asp Leu Glu Arg Lys Val Glu Ser Leu Gln Glu Glu
1               5                   10                  15

<210> SEQ ID NO 63
<211> LENGTH: 15
<212> TYPE: PRT
<213> ORGANISM: Homo sapiens

<400> SEQUENCE: 63

Asp Val Arg Gln Gln Tyr Glu Ser Val Ala Ala Lys Asn Leu Gln
1               5                   10                  15

<210> SEQ ID NO 64
<211> LENGTH: 15
<212> TYPE: PRT
<213> ORGANISM: Homo sapiens

<400> SEQUENCE: 64

Tyr Lys Ser Lys Phe Ala Asp Leu Ser Glu Ala Ala Asn Arg Asn
1               5                   10                  15

<210> SEQ ID NO 65
<211> LENGTH: 15
<212> TYPE: PRT
<213> ORGANISM: Homo sapiens

<400> SEQUENCE: 65

Ser Thr Glu Tyr Arg Arg Gln Val Gln Ser Leu Thr Cys Glu Val
1               5                   10                  15

<210> SEQ ID NO 66
<211> LENGTH: 15
<212> TYPE: PRT
<213> ORGANISM: Homo sapiens

<400> SEQUENCE: 66

Phe Ala Val Glu Ala Ala Asn Tyr Gln Asp Thr Ile Gly Arg Leu
1               5                   10                  15

<210> SEQ ID NO 67
<211> LENGTH: 15
<212> TYPE: PRT
<213> ORGANISM: Homo sapiens

<400> SEQUENCE: 67

Arg Glu Tyr Gln Asp Leu Leu Asn Val Lys Met Ala Leu Asp Ile
1               5                   10                  15

<210> SEQ ID NO 68
<211> LENGTH: 15
<212> TYPE: PRT
<213> ORGANISM: Homo sapiens

<400> SEQUENCE: 68

Met Ala Leu Asp Ile Glu Ile Ala Thr Tyr Arg Lys Leu Leu Glu
1               5                   10                  15

<210> SEQ ID NO 69
<211> LENGTH: 15
<212> TYPE: PRT
<213> ORGANISM: Homo sapiens

<400> SEQUENCE: 69

Arg Lys Leu Leu Glu Gly Glu Glu Ser Arg Ile Ser Leu Pro Leu
1               5                   10                  15

<210> SEQ ID NO 70
<211> LENGTH: 15
<212> TYPE: PRT
<213> ORGANISM: Homo sapiens

<400> SEQUENCE: 70

Gly Gln Val Ile Asn Glu Thr Ser Gln His His Asp Asp Leu Glu
1               5                   10                  15

<210> SEQ ID NO 71
<211> LENGTH: 15
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (12)..(13)
<223> OTHER INFORMATION: Citrulline

<400> SEQUENCE: 71

Met Ser Thr Xaa Ser Val Ser Ser Ser Tyr Xaa Xaa Met Phe
1               5                   10                  15

<210> SEQ ID NO 72
<211> LENGTH: 15
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Citrulline
<220> FEATURE:
<221> NAME/KEY: MOD_RES
<222> LOCATION: (13)..(13)
<223> OTHER INFORMATION: Citrulline

<400> SEQUENCE: 72

Tyr Xaa Xaa Met Phe Gly Gly Pro Gly Thr Ala Ser Xaa Pro Ser
1               5                   10                  15

<210> SEQ ID NO 73
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Citrulline
<220> FEATURE:
<221> NAME/KEY: MOD_RES
<222> LOCATION: (11)..(11)
<223> OTHER INFORMATION: Citrulline

<400> SEQUENCE: 73

Ser Ser Xaa Ser Tyr Val Thr Thr Ser Thr Xaa Thr Tyr Ser Leu
1               5                   10                  15

<210> SEQ ID NO 74
<211> LENGTH: 15
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Citrulline
<220> FEATURE:
<221> NAME/KEY: MOD_RES
<222> LOCATION: (15)..(15)
<223> OTHER INFORMATION: Citrulline

<400> SEQUENCE: 74

Val Thr Thr Ser Thr Xaa Thr Tyr Ser Leu Gly Ser Ala Leu Xaa
1               5                   10                  15

<210> SEQ ID NO 75
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (14)..(14)
<223> OTHER INFORMATION: Citrulline

<400> SEQUENCE: 75

Ser Pro Gly Gly Val Tyr Ala Thr Xaa Ser Ser Ala Val Xaa Leu
1               5                   10                  15

<210> SEQ ID NO 76
<211> LENGTH: 15
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (11)..(11)
<223> OTHER INFORMATION: Citrulline

```
<400> SEQUENCE: 76

Tyr Ala Thr Xaa Ser Ser Ala Val Xaa Leu Xaa Ser Ser Val Pro
1               5                   10                  15

<210> SEQ ID NO 77
<211> LENGTH: 15
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (6)..(6)
<223> OTHER INFORMATION: Citrulline
<220> FEATURE:
<221> NAME/KEY: MOD_RES
<222> LOCATION: (13)..(13)
<223> OTHER INFORMATION: Citrulline

<400> SEQUENCE: 77

Ser Ala Val Xaa Leu Xaa Ser Ser Val Pro Gly Val Xaa Leu Leu
1               5                   10                  15

<210> SEQ ID NO 78
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Citrulline

<400> SEQUENCE: 78

Gly Val Xaa Leu Leu Gln Asp Ser Val Asp Phe Ser Leu Ala Asp
1               5                   10                  15

<210> SEQ ID NO 79
<211> LENGTH: 15
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Citrulline

<400> SEQUENCE: 79

Phe Lys Asn Thr Xaa Thr Asn Glu Lys Val Glu Leu Gln Glu Leu
1               5                   10                  15

<210> SEQ ID NO 80
<211> LENGTH: 15
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Citrulline

<400> SEQUENCE: 80

Leu Leu Ala Glu Leu Glu Gln Leu Lys Gly Gln Gly Lys Ser Xaa
1               5                   10                  15

<210> SEQ ID NO 81
<211> LENGTH: 15
<212> TYPE: PRT
<213> ORGANISM: Homo sapiens
<220> FEATURE:
```

```
<221> NAME/KEY: MOD_RES
<222> LOCATION: (2)..(2)
<223> OTHER INFORMATION: Citrulline
<220> FEATURE:
<221> NAME/KEY: MOD_RES
<222> LOCATION: (12)..(12)
<223> OTHER INFORMATION: Citrulline

<400> SEQUENCE: 81

Phe Xaa Gln Asp Val Asp Asn Ala Ser Leu Ala Xaa Leu Asp Leu
 1               5                  10                  15

<210> SEQ ID NO 82
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Citrulline
<220> FEATURE:
<221> NAME/KEY: MOD_RES
<222> LOCATION: (12)..(12)
<223> OTHER INFORMATION: Citrulline

<400> SEQUENCE: 82

Asp Asn Ala Ser Leu Ala Xaa Leu Asp Leu Glu Xaa Lys Val Glu
 1               5                  10                  15

<210> SEQ ID NO 83
<211> LENGTH: 15
<212> TYPE: PRT
<213> ORGANISM: Homo sapiens
<220> FEATURE:
<221> NAME/KEY: MOD_RES
<222> LOCATION: (5)..(6)
<223> OTHER INFORMATION: Citrulline

<400> SEQUENCE: 83

Ser Thr Glu Tyr Xaa Xaa Gln Val Gln Ser Leu Thr Cys Glu Val
 1               5                  10                  15

<210> SEQ ID NO 84
<211> LENGTH: 15
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Citrulline

<400> SEQUENCE: 84

Phe Ala Val Glu Ala Ala Asn Tyr Gln Asp Thr Ile Gly Xaa Leu
 1               5                  10                  15

<210> SEQ ID NO 85
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Citrulline

<400> SEQUENCE: 85

Xaa Glu Tyr Gln Asp Leu Leu Asn Val Lys Met Ala Leu Asp Ile
 1               5                  10                  15

<210> SEQ ID NO 86
```

```
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Citrulline
<220> FEATURE:
<221> NAME/KEY: MOD_RES
<222> LOCATION: (10)..(10)
<223> OTHER INFORMATION: Citrulline

<400> SEQUENCE: 86

Xaa Lys Leu Leu Glu Gly Glu Glu Ser Xaa Ile Ser Leu Pro Leu
1               5                  10                  15

<210> SEQ ID NO 87
<211> LENGTH: 15
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Citrulline
<220> FEATURE:
<221> NAME/KEY: MOD_RES
<222> LOCATION: (15)..(15)
<223> OTHER INFORMATION: Citrulline

<400> SEQUENCE: 87

Thr His Ser Lys Xaa Thr Leu Leu Ile Lys Thr Val Glu Thr Xaa
1               5                  10                  15
```